(12) United States Patent
Whiteford et al.

(10) Patent No.: US 10,766,942 B2
(45) Date of Patent: Sep. 8, 2020

(54) FRAGMENTS OF SYNDECAN-2 HAVING ANTI-ANGIOGENIC ACTIVITY

(71) Applicant: Queen Mary University of London, London (GB)

(72) Inventors: James Whiteford, London (GB); Giulia De Rossi, London (GB)

(73) Assignee: Queen Mary University of London, London (GB)

( * ) Notice: Subject to any disclaimer, the term of this patent is extended or adjusted under 35 U.S.C. 154(b) by 0 days.

(21) Appl. No.: 15/520,149

(22) PCT Filed: Oct. 20, 2015

(86) PCT No.: PCT/GB2015/053130
§ 371 (c)(1),
(2) Date: Apr. 19, 2017

(87) PCT Pub. No.: WO2016/063042
PCT Pub. Date: Apr. 28, 2016

(65) Prior Publication Data
US 2017/0320929 A1    Nov. 9, 2017

(30) Foreign Application Priority Data

Oct. 20, 2014   (GB) .................................. 1418562.3

(51) Int. Cl.
| | | |
|---|---|---|
| *A61K 38/16* | (2006.01) | |
| *A61K 38/10* | (2006.01) | |
| *A61K 38/00* | (2006.01) | |
| *A61K 48/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07H 21/04* | (2006.01) | |
| *C12N 15/00* | (2006.01) | |
| *C12N 5/00* | (2006.01) | |
| *C07K 14/705* | (2006.01) | |
| *C07K 14/78* | (2006.01) | |
| *C07K 14/00* | (2006.01) | |

(52) U.S. Cl.
CPC ............ *C07K 14/705* (2013.01); *C07K 14/78* (2013.01); *A61K 38/00* (2013.01); *C07K 14/00* (2013.01)

(58) Field of Classification Search
None
See application file for complete search history.

(56) References Cited

U.S. PATENT DOCUMENTS 7,713,925 B2    5/2010   Ekker et al.
7,745,391 B2 *  6/2010   Mintz ..................... G06F 19/24
                                                    514/19.3

2007/0054332 A1   3/2007   Rapraeger et al.
2008/0020979 A1 * 1/2008   Rapraeger ............ C07K 14/705
                                                    514/1.9
2009/0005295 A1   1/2009   Ekker et al.

FOREIGN PATENT DOCUMENTS

WO        9500633        1/1995
WO        2014168548     10/2014

OTHER PUBLICATIONS

Tokuriki et al. 2009. Current Opin. Structural Biol. 19:596-604 (Year: 2009).*
Bhattacharya et al 2017. PLOS One 12:e-0171355 (Year: 2017).*
Guo et al. 2004, PNAS USA 101(25):9205-10 (Year: 2004).*
Uniprot B4DT61 (2008). (Year: 2008).*
Kim et al. 2007. Mol. Cancer Ther. 6:1785 (Year: 2007).*
Beauvais et al., "The syndecan-1 ectodomain regulates alphavbeta3 integrin activity in human mammary carcinoma cells", 2004, Journal of cell biology, 167, p. 171-181.
Beauvais et al., "Syndecan-1 regulates alphavbeta3 and alphavbeta5 integrin activation during angiogenesis and is blocked by synstatin, a novel peptide inhibitor", 2009, Journal of experimental medicine, 206, p. 691-705.
Beauvais et al., "Syndecan-1 couples the insulin-like growth factor-1 receptor to inside-out integrin activation", 2010, Journal of cell science, 123, p. 3796-3807.
Carmeliet, "Angiogenesis in health and disease", 2003, Nature medicine, 9, p. 653-660.
De Rossi et al., "Critical Factors in Measuring Angiogenesis Using the Aortic Ring Model", 2013, Journal of genetic syndrome & gene therapy, 4, 1000147.
De Rossi et al., "Novel insight into the biological functions of syndecan ectodomain core proteins", 2013, BioFactors. 39, p. 374-382.
De Rossi et al., "A novel role for syndecan-3 in angiogenesis",2013, 20 F1000Research, 2, 270.
Fears et al., "Syndecan-2 is expressed in the microvasculature of 25 gliomas and regulates angiogenic processes in microvascular endothelial cells", 2006, Journal of biological chemistry, 281, p. 14533-14536.
Ishiguro et al., "Syndecan-4 as a molecule involved in defense mechanisms", 2002, Glycoconjugate, 19, p. 315-318.

(Continued)

*Primary Examiner* — Shulamith H Shafer
(74) *Attorney, Agent, or Firm* — Stradley Ronon Stevens & Young, LLP

(57) ABSTRACT

The present invention provides an anti-angiogenic peptide comprising an amino acid sequence having at least 70% identity to amino acid residues 123-140 of SEQ ID NO 1 or amino acid residues 24-141 of SEQ ID NO 2. The invention also provides nucleic acid constructs encoding such peptides, and vectors and cells comprising such nucleic acid constructs. The invention further provides pharmaceutical compositions comprising the peptides or nucleic acid constructs of the invention, and the use of peptides, nucleic acid constructs or pharmaceutical compositions of the invention to treat diseases associated with angiogenesis.10

21 Claims, 14 Drawing Sheets

Specification includes a Sequence Listing.

(56) References Cited

OTHER PUBLICATIONS

Kwon et al., "Interleukin-lalpha promotes extracellular shedding of syndecan-2 via induction of matrix metalloproteinase-7 expression", 2014, Biochemical and biophysical research communications, 446, p. 487-492.

Manon-Jensen et al., "Proteoglycans in health and disease: the multiple roles of syndecan shedding", 2010, FEBS journal, 277, p. 3876-3889.

Manon-Jensen et al., "Mapping of MMP cleavage sites on syndecan-1 and syndecan-4 ectodomains", 2013, FEBS journal, 280, p. 2320-2331.

McFall et al. "Identification of an adhesion site within the syndecan-4 extracellular protein domain", 1997, Journal of biological chemistry, 272, p. 12901-12904.

Preussmeyer et al. 2010. A disintegrin and metalloproteinase 17 (ADAM17) mediates inflammation-induced shedding of syndecan-1 and -4 by lung epithelial cells. The Journal of biological chemistry. 285:555-564.

Rapraeger et al., "Vascular endothelial-cadherin stimulates syndecan-I-coupled insulin-like growth factor-1 receptor and cross-talk between alphaVbeta3 integrin and vascular endothelial growth factor receptor 2 at the onset of endothelial cell dissemination during angiogenesis", 2013, FEBS journal, 280, p. 2194-2206.

Reynolds et al., "Enhanced pathological angiogenesis in mice lacking beta(3) integrin or beta(3) and beta(5) integrins", 2002, Nature medicine, 8, p. 27-34.

Takahashi et al., "A mutant receptor tyrosine phosphatase, CD148, causes defects in vascular development", 2003, Molecular and cellular biology, 23, p. 1817-1831.

Takahashi et al., "A monoclonal antibody against CD148, a receptor-like tyrosine phosphatase, inhibits endothelial-cell growth and angiogenesis", 2006, Blood, 108, p. 1234-1242.

Trapasso et al., "Genetic ablation of Ptprj, a mouse cancer susceptibility gene, results in normal growth and development and does not predispose to spontaneous tumorigenesis", 2006, DNA and cell biology, 25, p. 376-382.

Whiteford et al., "Syndecan-2 is a novel ligand for the protein tyrosine phosphatase receptor CD148", 2011, Molecular biology of the cell, 22, p. 3609-3624.

Okina et al., "Syndecan proteoglycan contributions to cytoskeletal organization and contractility", 2009, Scandinavian journal of medicine & science in sports, 19, p. 479-489.

Alexopoulou et al., "Syndecans in wound healing, inflammation and vascular biology", 2007, International journal of biochemistry & cell biology, 39, p. 505-528.

McQuade et al., "Syndecan-1 regulates alphavbeta5 integrin activity in B82L fibroblasts", 2006, Journal of cell science, 119, p. 2445-2456.

Noguer et al., "Syndecan-2 downregulation impairs angiogenesis in human microvascular endothelial cells", 2009, Experimental cell research, 315, p. 795-808.

Chen et al., "Syndecan-2 is essential for angiogenic sprouting during zebrafish development", 2004, Blood, 103, p. 1710-1719.

Uniprot F7A963.

Uniprot Q99L05.

Uniprot E5RJB8.

Whiteford et al., "Syndecans promote integrin-mediated adhesion of mesenchymal cells in two distinct pathways", 2007, Experimental cell research, 313, p. 3902-3913.

Whiteford et al., "A conserved NXIP motif is required for cell adhesion properties of the syndecan-4 ectodomain", 2006, Journal of biological chemistry, 281, p. 32156-32163.

McFall et al., "Characterization of the high affinity cell-binding domain in the cell surface proteoglycan syndecan-4", 1998, Journal of biological chemistry, 273, p. 28270-28276.

Fukuhara et al. 2010. Biochemistry, vol. 82, No. 4, pp. 290-301.

* cited by examiner

A)
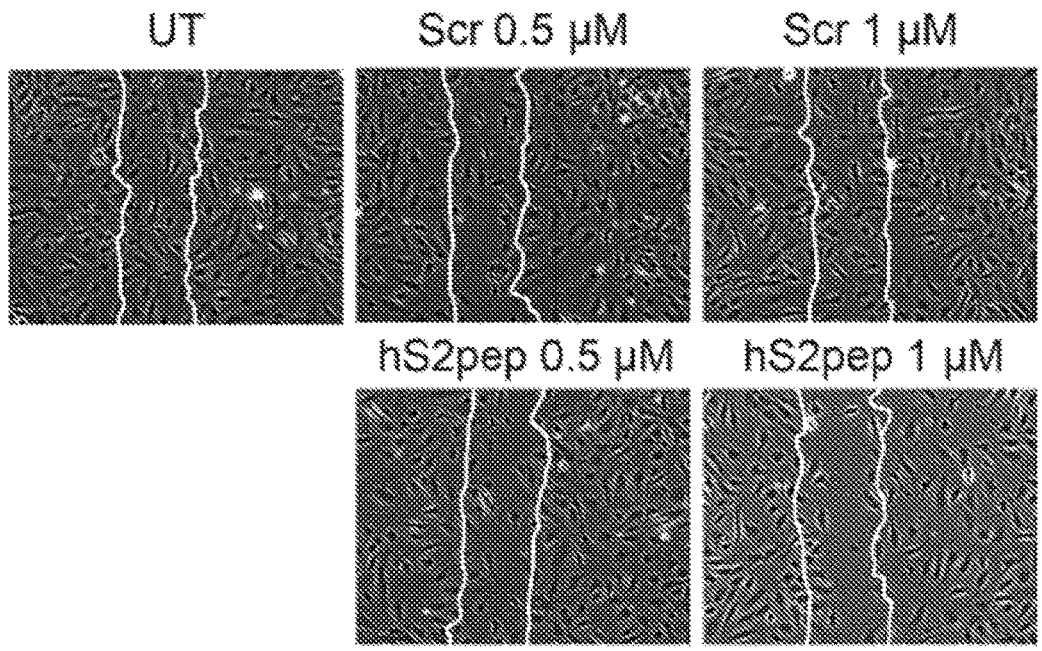
B)
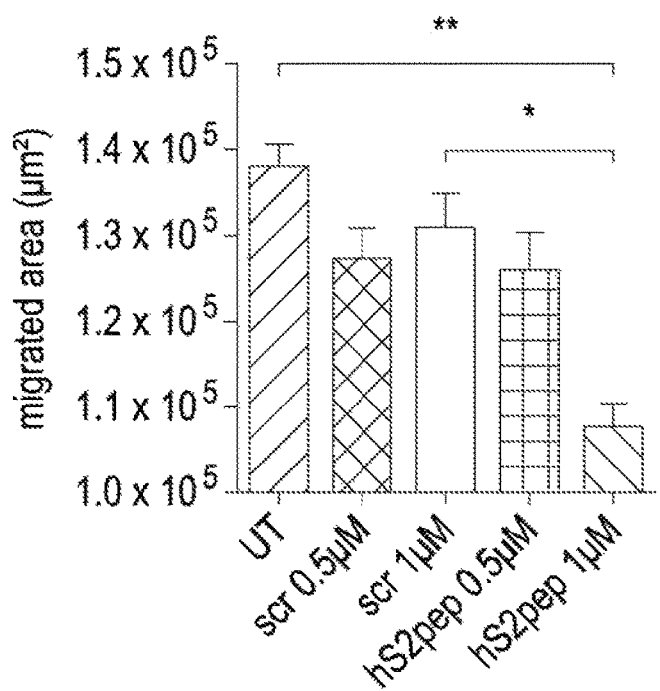
Fig. 1

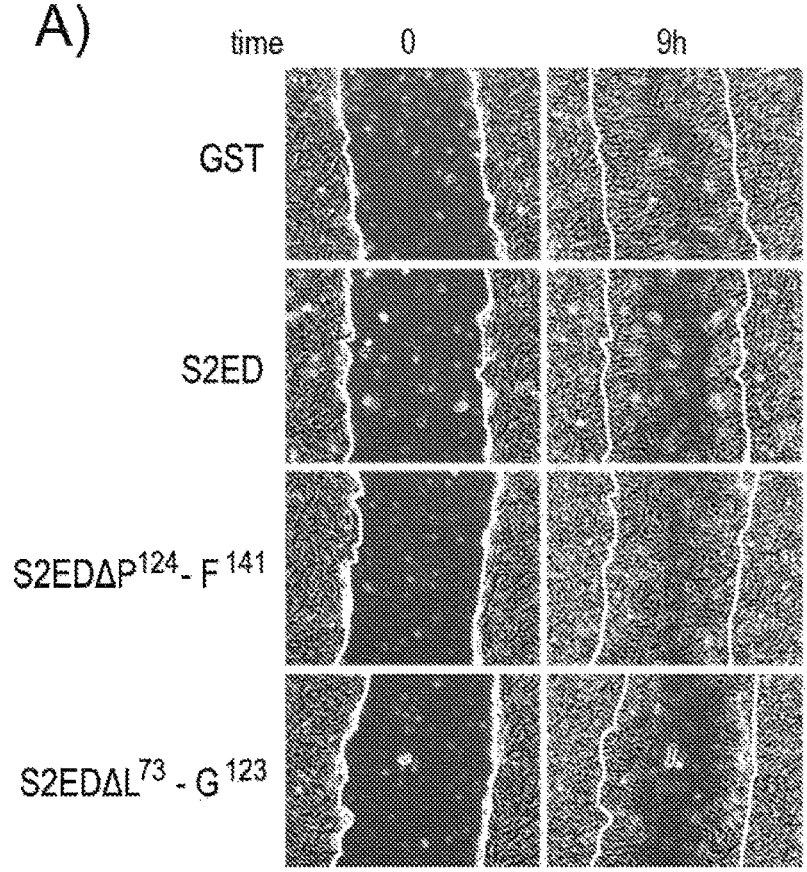
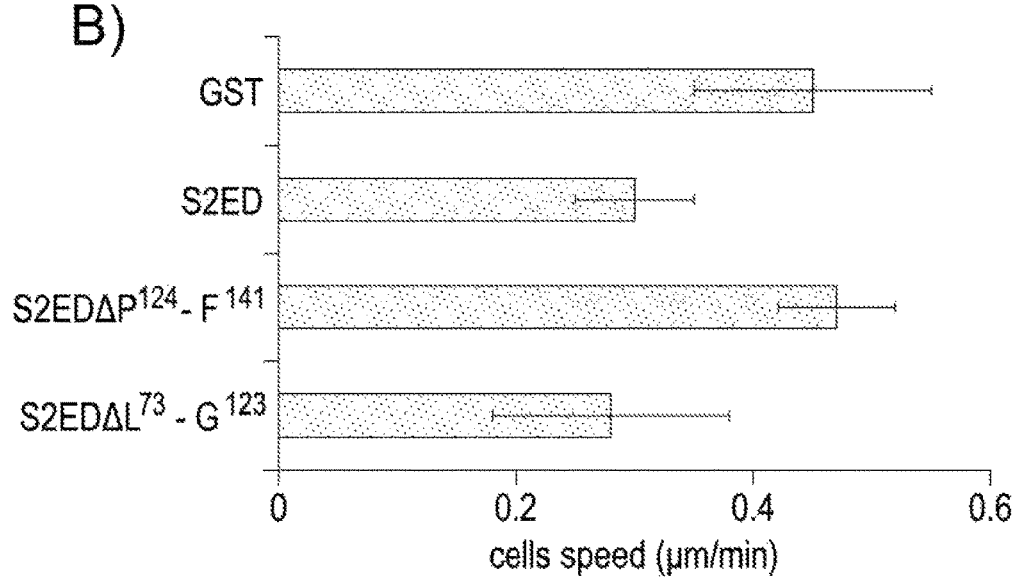
Fig. 2

A)
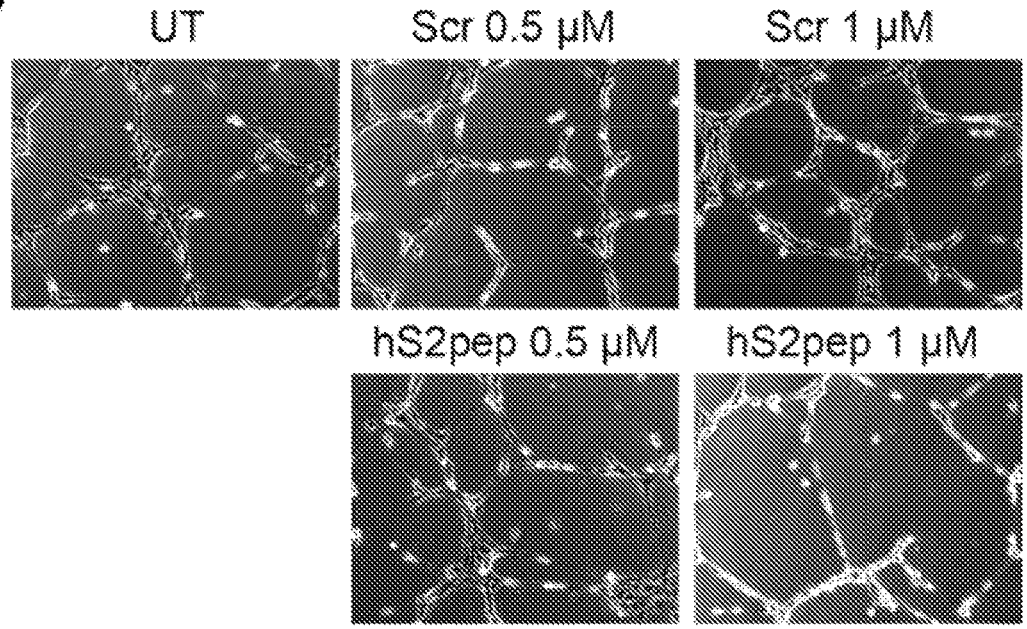
B)
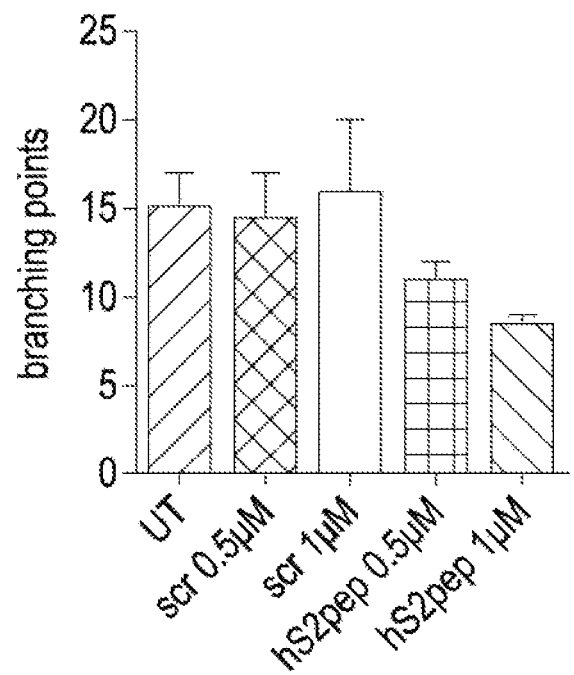
Fig. 3

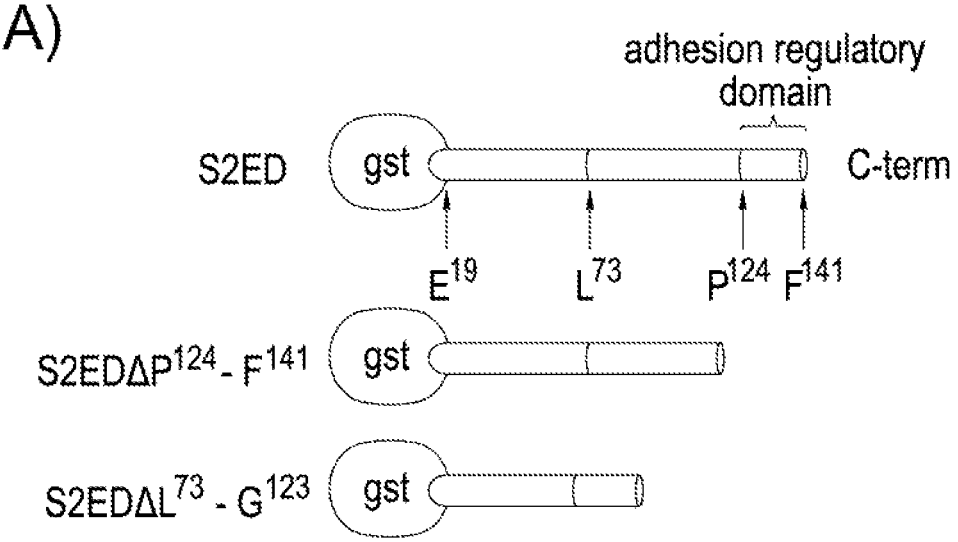
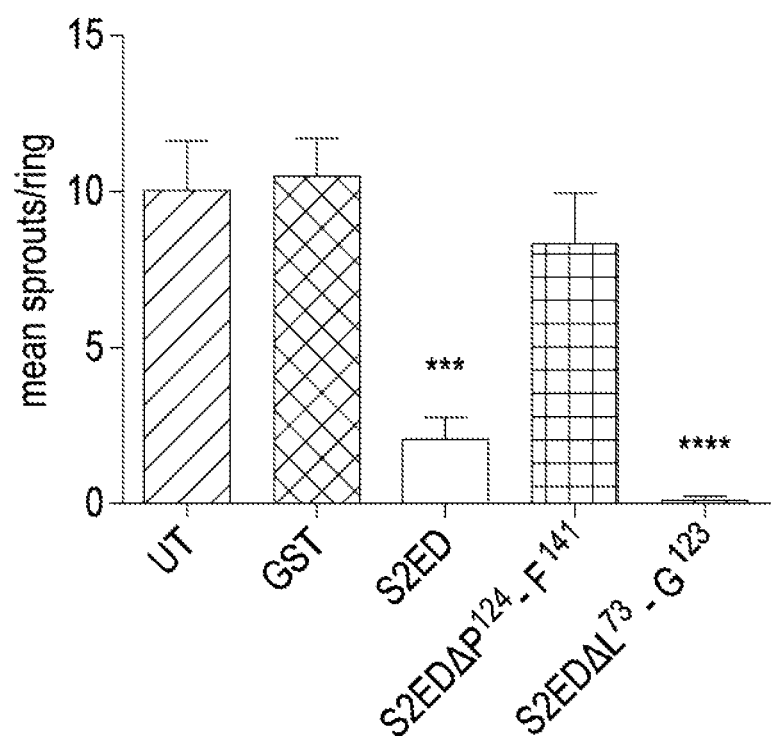
Fig. 4

A)
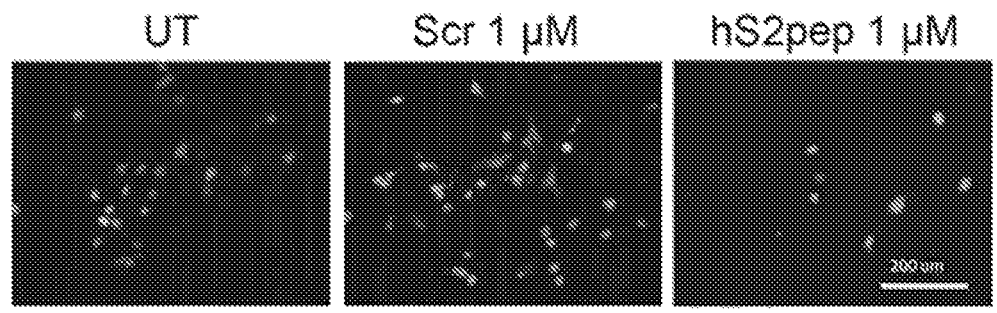
B)
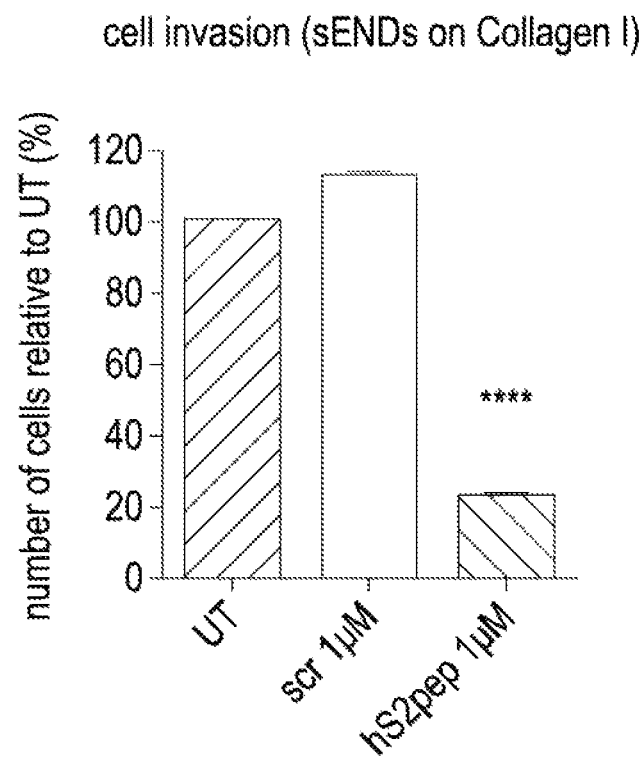
Fig. 5

A)
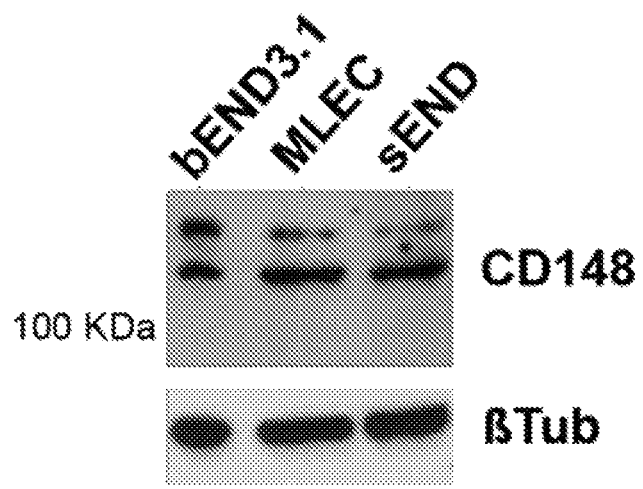
B)
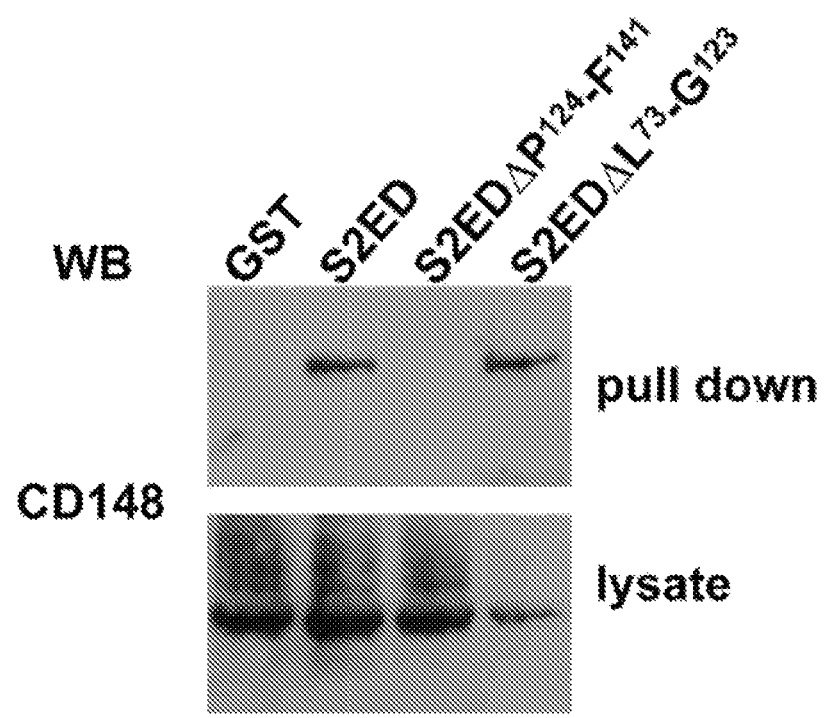
Fig. 6

SEQ ID NO 1

HUMAN syndecan-2

1     mrrawilltl glvacvsaes raeltsdkdm yldnssieea sgvypidddd yasasgsgad
61    edvespeltt srplpkillt saapkvettt lniqnkipaq tkspeetdke kvhlsdserk
121   mdpaeedtnv ytekhsdslf krtevlaavi aggvigflfa iflilllvyr mrkkdegsyd
181   lgerkpssaa yqkaptkefy a

SEQ ID NO 2

MOUSE Syndecan-2

1     mqrawilltl glmacvsaet rteltsdkdm yldnssieea sgvypidddd yssasgsgad
61    ediespvltt sqlipriplt saaspkvetm tlktqsitpa qtespeetdk eevdiseaee
121   klqpaikstd vytekhsdnl fkrtevlaav iaggvigflf aiflilllvy rmrkkdegsy
181   dlgerkpssa ayqkaptkef ya

SEQ ID NO 3

>S2ED
1     MSPILGYWKI KGLVQPTRLL LEYLEEKYEE HLYERDEGDK WRNKKFELGL EFPNLPYYID
61    GDVKLTQSMA IIRYIADKHN MLGGCPKERA EISMLEGAVL DIRYGVSRIA YSKDFETLKV
121   DFLSKLPEML KMFEDRLCHK TYLNGDHVTH PDFMLYDALD VVLYMDPMCL DAFPKLVCFK
181   KRIEAIPQID KYLKSSKYIA WPLQGWQATF GGGDHPPKSD GSTSGSGHHH HHHSAGLVPR
241   GSTAIGMKET AAAKFERQHM DSPDLGTGGG SGDDDDKETR TELTSDKDMY LDNSSIEEAS
301   GVYPIDDDDY SSASGSGADE DIESPVLTTS QLIPRIPLTS AASPKVETMT LKTQSITPAQ
361   TESPEETDKE EVDISEAEEK LGPAIKSTDV YTEKHSDNLF *

<u>GST + linker</u>
18aa peptide

Fig. 7

SEQ ID NO 4

>S2EDΔP124-F141

| | |
|---|---|
| 1 | MSPILGYWKI KGLVQPTRLL LEYLEEKYEE HLYERDEGDK WRNKKFELGL EFPNLPYYID |
| 61 | GDVKLTQSMA IIRYIADKHN MLGGCPKERA EISMLEGAVL DIRYGVSRIA YSKDFETLKV |
| 121 | DFLSKLPEML KMFEDRLCHK TYLNGDHVTH PDFMLYDALD VVLYMDPMCL DAFPKLVCFK |
| 181 | KRIEAIPQID KYLKSSKYIA WPLQGWQATF GGGDHPPKSD GSTSGSGHHH HHHSAGLVPR |
| 241 | GSTAIGMKET AAAKFERQHM DSPDLGTGGG SGDDDDKETR TELTSDKDMY LDNSSIEEAS |
| 301 | GVYPIDDDDY SSASGSGADE DIESPVLTTS QLIPRIPLTS AASPKVETMT LKTQSITPAQ |
| 361 | TESPEETDKE EVDISEAEEK LG* |

GST + linker

SEQ ID NO 5

>S2EDΔL73-G123

| | |
|---|---|
| 1 | MSPILGYWKI KGLVQPTRLL LEYLEEKYEE HLYERDEGDK WRNKKFELGL EFPNLPYYID |
| 61 | GDVKLTQSMA IIRYIADKHN MLGGCPKERA EISMLEGAVL DIRYGVSRIA YSKDFETLKV |
| 121 | DFLSKLPEML KMFEDRLCHK TYLNGDHVTH PDFMLYDALD VVLYMDPMCL DAFPKLVCFK |
| 181 | KRIEAIPQID KYLKSSKYIA WPLQGWQATF GGGDHPPKSD GSTSGSGHHH HHHSAGLVPR |
| 241 | GSTAIGMKET AAAKFERQHM DSPDLGTGGG SGDDDDKETR TELTSDKDMY LDNSSIEEAS |
| 301 | GVYPIDDDDY SSASGSGADE DIESPVLTTS QPAIKSTDVY TEKHSDNLF* |

GST + linker
18aa peptide

SEQ ID NO 6 hS2pep

PAEEDTNVYTEKHSDSLF

SEQ ID NO 7

Scr

VPYFNATLTDEESSDKET

SEQ ID NO 8
Human syndecan-2 cDNA coding sequence

```
  1 atgcggcgcg cgtggatcct gctcaccttg ggcttggtgg cctgcgtgtc
 51 ggcggagtcg agagcagagc tgacatctga taaagacatg taccttgaca
101 acagctccat tgaagaagct tcaggagtgt atcctattga tgacgatgac
151 tacgcttctg cgtctggctc gggagctgat gaggatgtag agagtccaga
201 gctgacaaca tctcgaccac ttccaaagat actgttgact agtgctgctc
251 caaaagtgga accacgacg ctgaatatac agaacaagat acctgctcag
301 acaaagtcac ctgaagaaac tgataaagag aaagttcacc tctctgactc
351 agaaaggaaa atggaccag ccgaagagga tacaaatgtg tatactgaga
401 aacactcaga cagtctgttt aaacggacag aagtcctagc agctgtcatt
451 gctggtggag ttattggctt tctctttgca attttctta tcctgctgtt
501 ggtgtatcgc atgagaaaga aggatgaagg aagctatgac cttggagaac
551 gcaaaccatc cagtgctgct tatcagaagg cacctactaa ggagttttat
601 gcgtaa
```
DNA corresponding to peptide of the invention SEQ ID NO 9
Murine Syndecan-2 coding sequence

```
  1 atgcagcgcg cgtggatcct gctcaccttg ggcttgatgg cctgtgtgtc
 51 cgcagagacg agaacagagc tgacatccga taaggatatg taccttgaca
101 atagctccat tgaggaagct tcaggagtat atcctattga tgatgatgac
151 tattcttctg cctcaggctc aggagctgat gaagacatag agagtccagt
201 tctgacaaca tcccaactga ttccaagaat cccactcact agtgctgctt
251 cccccaaagt ggaaaccatg acgttgaaga cacaaagcat tacacctgct
301 cagactgagt cacctgaaga aactgacaag gaggaagttg acatttctga
351 ggcagaagag aagctgggcc ctgctataaa aagcacagat gtgtacacgg
401 agaaacattc agacaatctg tttaaacgga cagaagttct agcagccgtc
451 attgctggtg gtgtgatcgg ctttctcttt gccattttcc tcatcctgct
501 attggtgtac cgcatgcgga agaaagatga aggaagctac gaccttggag
551 aacgcaaacc atccagcgca gcttaccaga aggcacccac taaggagttt
601 tatgcataa
```
DNA corresponding to peptide of the invention

Fig. 8

SEQ ID NO 10

>S2ED
```
   1 atgtcccta tactaggtta ttggaaaatt aagggccttg tgcaacccac
  51 tcgacttctt ttggaatatc ttgaagaaaa atatgaagag catttgtatg
 101 agcgcgatga aggtgataaa tggcgaaaca aaaagtttga attgggtttg
 151 gagtttccca atcttcctta ttatattgat ggtgatgtta aattaacaca
 201 gtctatggcc atcatacgtt atatagctga caagcacaac atgttgggtg
 251 gttgtccaaa agagcgtgca gagatttcaa tgcttgaagg agcggttttg
 301 gatattagat acggtgtttc gagaattgca tatagtaaag actttgaaac
 351 tctcaaagtt gattttctta gcaagctacc tgaaatgctg aaaatgttcg
 401 aagatcgttt atgtcataaa acatatttaa atggtgatca tgtaacccat
 451 cctgacttca tgttgtatga cgctcttgat gttgttttat acatggaccc
 501 aatgtgcctg gatgcgttcc caaaattagt ttgttttaaa aaacgtattg
 551 aagctatccc acaaattgat aagtacttga atccagcaa gtatatagca
 601 tggcctttgc agggctggca agccacgttt ggtggtggcg accatcctcc
 651 aaaatcggat ggttcaacta gtggttctgg tcatcaccat caccatcact
 701 ccgcgggtct ggtgccacgc ggtagtactg caattggtat gaaagaaacc
 751 gctgctgcta aattcgaacg ccagcacatg gacagcccag atctgggtac
 801 cggtggtggc tccggtgatg acgacgacaa ggagacgaga acagagctga
 851 catccgataa ggatatgtac cttgacaata gctccattga ggaagcttca
 901 ggagtatatc ctattgatga tgatgactat tcttctgcct caggctcagg
 951 agctgatgaa gacatagaga gtccagttct gacaacatcc caacctgcta
1001 taaaagcac agatgtgtac acggagaaac attcagacaa tctgttttaa
```

Fig. 8 (continued)

SEQ ID NO 11

\>S2EDΔP124-F141

```
   1 atgtcccta tactaggtta ttggaaaatt aagggccttg tgcaacccac
  51 tcgacttctt ttggaatatc ttgaagaaaa atatgaagag catttgtatg
 101 agcgcgatga aggtgataaa tggcgaaaca aaaagtttga attgggtttg
 151 gagtttccca atcttcctta ttatattgat ggtgatgtta aattaacaca
 201 gtctatggcc atcatacgtt atatagctga caagcacaac atgttgggtg
 251 gttgtccaaa agagcgtgca gagatttcaa tgcttgaagg agcggttttg
 301 gatattagat acggtgtttc gagaattgca tatagtaaag actttgaaac
 351 tctcaaagtt gattttctta gcaagctacc tgaaatgctg aaaatgttcg
 401 aagatcgttt atgtcataaa acatatttaa atggtgatca tgtaacccat
 451 cctgacttca tgttgtatga cgctcttgat gttgttttat acatggaccc
 501 aatgtgcctg gatgcgttcc caaaattagt ttgttttaaa aaacgtattg
 551 aagctatccc acaaattgat aagtacttga atccagcaa gtatatagca
 601 tggcctttgc agggctggca agccacgttt ggtggtggcg accatcctcc
 651 aaaatcggat ggttcaacta gtggttctgg tcatcaccat caccatcact
 701 ccgcgggtct ggtgccacgc ggtagtactg caattggtat gaaagaaacc
 751 gctgctgcta aattcgaacg ccagcacatg gacagcccag atctgggtac
 801 cggtggtggc tccggtgatg acgacgacaa ggagacgaga acagagctga
 851 catccgataa ggatatgtac cttgacaata gctccattga ggaagcttca
 901 ggagtatatc ctattgatga tgatgactat tcttctgcct caggctcagg
 951 agctgatgaa gacatagaga gtccagttct gacaacatcc caactgattc
1001 caagaatccc actcactagt gctgcttccc ccaaagtgga aaccatgacg
1051 ttgaagacac aaagcattac acctgctcag actgagtcac ctgaagaaac
1101 tgacaaggag gaagttgaca tttctgaggc agaagagaag ctgggctaa
```

Fig. 8 (continued)

SEQ ID NO 12

>S2EDAL73-G123
```
   1 atgtcccta tactaggtta ttggaaaatt aagggccttg tgcaacccac
  51 tcgacttctt ttggaatatc ttgaagaaaa atatgaagag catttgtatg
 101 agcgcgatga aggtgataaa tggcgaaaca aaagtttga attgggtttg
 151 gagtttccca atcttcctta ttatattgat ggtgatgtta aattaacaca
 201 gtctatggcc atcatacgtt atatagctga caagcacaac atgttgggtg
 251 gttgtccaaa agagcgtgca gagatttcaa tgcttgaagg agcggttttg
 301 gatattagat acggtgtttc gagaattgca tatagtaaag actttgaaac
 351 tctcaaagtt gattttctta gcaagctacc tgaaatgctg aaaatgttcg
 401 aagatcgttt atgtcataaa acatatttaa atggtgatca tgtaacccat
 451 cctgacttca tgttgtatga cgctcttgat gttgttttat acatggaccc
 501 aatgtgcctg gatgcgttcc caaaattagt ttgttttaaa aaacgtattg
 551 aagctatccc acaaattgat aagtacttga atccagcaa gtatatagca
 601 tggcctttgc agggctggca agccacgttt ggtggtggcg accatcctcc
 651 aaaatcggat ggttcaacta gtggttctgg tcatcaccat caccatcact
 701 ccgcgggtct ggtgccacgc ggtagtactg caattggtat gaaagaaacc
 751 gctgctgcta aattcgaacg ccagcacatg gacagcccag atctgggtac
 801 cggtggtggc tccggtgatg acgacgacaa ggagacgaga acagagctga
 851 catccgataa ggatatgtac cttgacaata gtccattga ggaagcttca
 901 ggagtatatc ctattgatga tgatgactat tcttctgcct caggctcagg
 951 agctgatgaa gacatagaga gtccagttct gacaacatcc caacctgcta
1001 taaaaagcac agatgtgtac acggagaaac attcagacaa tctgttttaa
```

Fig. 8 (continued)

SEQUENCE LISTING

```
<160> NUMBER OF SEQ ID NOS: 12

<210> SEQ ID NO 1
<211> LENGTH: 201
<212> TYPE: PRT
<213> ORGANISM: Homo sapiens

<400> SEQUENCE: 1

Met Arg Arg Ala Trp Ile Leu Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

His Leu Ser Asp Ser Glu Arg Lys Met Asp Pro Ala Glu Glu Asp Thr
        115                 120                 125

Asn Val Tyr Thr Glu Lys His Ser Asp Ser Leu Phe Lys Arg Thr Glu
    130                 135                 140

Val Leu Ala Ala Val Ile Ala Gly Gly Val Ile Gly Phe Leu Phe Ala
145                 150                 155                 160

Ile Phe Leu Ile Leu Leu Val Tyr Arg Met Arg Lys Lys Asp Glu
                165                 170                 175

Gly Ser Tyr Asp Leu Gly Glu Arg Lys Pro Ser Ser Ala Ala Tyr Gln
            180                 185                 190

Lys Ala Pro Thr Lys Glu Phe Tyr Ala
        195                 200

<210> SEQ ID NO 2
<211> LENGTH: 202
<212> TYPE: PRT
<213> ORGANISM: Mus musculus

<400> SEQUENCE: 2
```

Met Gln Arg Ala Trp Ile Leu Leu Thr Leu Gly Leu Met Ala Cys Val
1               5                   10                  15

Ser Ala Glu Thr Arg Thr Glu Leu Thr Ser Asp Lys Asp Met Tyr Leu
            20                  25                  30

Asp Asn Ser Ser Ile Glu Glu Ala Ser Gly Val Tyr Pro Ile Asp Asp
                35                  40                  45

Asp Asp Tyr Ser Ser Ala Ser Gly Ser Gly Ala Asp Glu Asp Ile Glu
    50                  55                  60

Ser Pro Val Leu Thr Thr Ser Gln Leu Ile Pro Arg Ile Pro Leu Thr
65                  70                  75                  80

Ser Ala Ala Ser Pro Lys Val Glu Thr Met Thr Leu Lys Thr Gln Ser
                85                  90                  95

Ile Thr Pro Ala Gln Thr Glu Ser Pro Glu Glu Thr Asp Lys Glu Glu
            100                 105                 110

Val Asp Ile Ser Glu Ala Glu Leu Gly Pro Ala Ile Lys Ser
            115                 120                 125

Thr Asp Val Tyr Thr Glu Lys His Ser Asp Asn Leu Phe Lys Arg Thr
    130                 135                 140

Glu Val Leu Ala Ala Val Ile Ala Gly Gly Val Ile Gly Phe Leu Phe
145                 150                 155                 160

Ala Ile Phe Leu Ile Leu Leu Val Tyr Arg Met Arg Lys Lys Asp
                165                 170                 175

Glu Gly Ser Tyr Asp Leu Gly Glu Arg Lys Pro Ser Ser Ala Ala Tyr
            180                 185                 190

Gln Lys Ala Pro Thr Lys Glu Phe Tyr Ala
            195                 200

<210> SEQ ID NO 3
<211> LENGTH: 400
<212> TYPE: PRT
<213> ORGANISM: Artificial sequence
<220> FEATURE:
<223> OTHER INFORMATION: S2ED
<220> FEATURE:
<221> NAME/KEY: GST + Linker
<222> LOCATION: (1)..(277)
<220> FEATURE:
<221> NAME/KEY: 18 amino acid peptide
<222> LOCATION: (383)..(400)

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

```
Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Glu Thr Arg Thr Glu Leu Thr Ser Asp Lys Asp
275                 280                 285

Met Tyr Leu Asp Asn Ser Ser Ile Glu Glu Ala Ser Gly Val Tyr Pro
290                 295                 300

Ile Asp Asp Asp Asp Tyr Ser Ser Ala Ser Gly Ser Gly Ala Asp Glu
305                 310                 315                 320

Asp Ile Glu Ser Pro Val Leu Thr Thr Ser Gln Leu Ile Pro Arg Ile
                325                 330                 335

Pro Leu Thr Ser Ala Ala Ser Pro Lys Val Glu Thr Met Thr Leu Lys
            340                 345                 350

Thr Gln Ser Ile Thr Pro Ala Gln Thr Glu Ser Pro Glu Glu Thr Asp
        355                 360                 365

Lys Glu Glu Val Asp Ile Ser Glu Ala Glu Glu Lys Leu Gly Pro Ala
    370                 375                 380

Ile Lys Ser Thr Asp Val Tyr Thr Glu Lys His Ser Asp Asn Leu Phe
385                 390                 395                 400

<210> SEQ ID NO 4
<211> LENGTH: 382
<212> TYPE: PRT
<213> ORGANISM: Artificial sequence
<220> FEATURE:
<223> OTHER INFORMATION: S2EDdeltaP124-F141
<220> FEATURE:
<221> NAME/KEY: GST + Linker
<222> LOCATION: (1)..(277)

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80
```

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Asp Asp Asp Asp Lys Glu Thr Arg Thr Glu Leu Thr Ser Asp Lys Asp
            275                 280                 285

Met Tyr Leu Asp Asn Ser Ser Ile Glu Glu Ala Ser Gly Val Tyr Pro
290                 295                 300

Ile Asp Asp Asp Asp Tyr Ser Ser Ala Ser Gly Ser Gly Ala Asp Glu
305                 310                 315                 320

Asp Ile Glu Ser Pro Val Leu Thr Thr Ser Gln Leu Ile Pro Arg Ile
                325                 330                 335

Pro Leu Thr Ser Ala Ala Ser Pro Lys Val Glu Thr Met Thr Leu Lys
            340                 345                 350

Thr Gln Ser Ile Thr Pro Ala Gln Thr Glu Ser Pro Glu Glu Thr Asp
            355                 360                 365

Lys Glu Glu Val Asp Ile Ser Glu Ala Glu Glu Lys Leu Gly
            370                 375                 380

<210> SEQ ID NO 5
<211> LENGTH: 349
<212> TYPE: PRT
<213> ORGANISM: Artificial sequence
<220> FEATURE:
<223> OTHER INFORMATION: S2EDdeltaL73-G123
<220> FEATURE:
<221> NAME/KEY: GST + Linker
<222> LOCATION: (1)..(277)
<220> FEATURE:
<221> NAME/KEY: 18 amino acid peptide
<222> LOCATION: (332)..(349)

<400> SEQUENCE: 5

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30
```

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Gly Ser Thr Ser
            210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
                260                 265                 270

Asp Asp Asp Asp Lys Glu Thr Arg Thr Glu Leu Thr Ser Asp Lys Asp
            275                 280                 285

Met Tyr Leu Asp Asn Ser Ser Ile Glu Glu Ala Ser Gly Val Tyr Pro
290                 295                 300

Ile Asp Asp Asp Tyr Ser Ser Ala Ser Gly Ser Gly Ala Asp Glu
305                 310                 315                 320

Asp Ile Glu Ser Pro Val Leu Thr Thr Ser Gln Pro Ala Ile Lys Ser
                325                 330                 335

Thr Asp Val Tyr Thr Glu Lys His Ser Asp Asn Leu Phe
            340                 345

<210> SEQ ID NO 6
<211> LENGTH: 18
<212> TYPE: PRT
<213> ORGANISM: Artificial sequence
<220> FEATURE:
<223> OTHER INFORMATION: hS2pep peptide derived from human syndecan-2

<400> SEQUENCE: 6

Pro Ala Glu Glu Asp Thr Asn Val Tyr Thr Glu Lys His Ser Asp Ser
1               5                   10                  15

Leu Phe

<210> SEQ ID NO 7
<211> LENGTH: 18
<212> TYPE: PRT

<213> ORGANISM: Artificial sequence
<220> FEATURE:
<223> OTHER INFORMATION: Scrambled peptide used as a negative control

<400> SEQUENCE: 7

Val Pro Tyr Phe Asn Ala Thr Leu Thr Asp Glu Glu Ser Ser Asp Lys
1               5                   10                  15

Glu Thr

<210> SEQ ID NO 8
<211> LENGTH: 606
<212> TYPE: DNA
<213> ORGANISM: Homo sapiens

<400> SEQUENCE: 8

```
atgcggcgcg cgtggatcct gctcaccttg ggcttggtgg cctgcgtgtc ggcggagtcg      60
agagcagagc tgacatctga taaagacatg taccttgaca cagctccat  tgaagaagct    120
tcaggagtgt atcctattga tgacgatgac tacgcttctg cgtctggctc gggagctgat    180
gaggatgtag agagtccaga gctgacaaca tctcgaccac ttccaaagat actgttgact    240
agtgctgctc caaaagtgga aaccacgacg ctgaatatac agaacaagat acctgctcag    300
acaaagtcac ctgaagaaac tgataaagag aaagttcacc tctctgactc agaaaggaaa    360
atggacccag ccgaagagga tacaaatgtg tatactgaga acactcaga  cagtctgttt    420
aaacggacag aagtcctagc agctgtcatt gctggtggag ttattggctt ctctctttgca   480
attttttctta tcctgctgtt ggtgtatcgc atgagaaaga aggatgaagg aagctatgac   540
cttggagaac gcaaaccatc cagtgctgct tatcagaagg cacctactaa ggagttttat   600
gcgtaa                                                               606
```

<210> SEQ ID NO 9
<211> LENGTH: 609
<212> TYPE: DNA
<213> ORGANISM: Mus musculus

<400> SEQUENCE: 9

```
atgcagcgcg cgtggatcct gctcaccttg ggcttgatgg cctgtgtgtc cgcagagacg      60
agaacagagc tgacatccga taaggatatg taccttgaca atagctccat gaggaagct     120
tcaggagtat atcctattga tgatgatgac tattcttctg cctcaggctc aggagctgat    180
gaagacatag agagtccagt tctgacaaca tcccaactga ttccaagaat cccactcact    240
agtgctgctt cccccaaagt ggaaaccatg acgttgaaga cacaaagcat tacacctgct    300
cagactgagt cacctgaaga aactgacaag gaggaagttg acatttctga ggcagaagag    360
aagctgggcc ctgctataaa aagcacagat gtgtacacgg agaaacattc agacaatctg    420
tttaaacgga cagaagttct agcagccgtc attgctggtg gtgtgatcgg ctttctcttt    480
gccattttcc tcatcctgct attggtgtac cgcatgcgga gaaagatga  aggaagctac    540
gaccttggag aacgcaaacc atccagcgca gcttaccaga aggcacccac taaggagttt    600
tatgcataa                                                            609
```

<210> SEQ ID NO 10
<211> LENGTH: 1050
<212> TYPE: DNA
<213> ORGANISM: Artificial sequence
<220> FEATURE:
<223> OTHER INFORMATION: DNA sequence of S2ED peptide used in the
      Examples

<400> SEQUENCE: 10

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg     300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtgatg acgacgacaa ggagacgaga    840
acagagctga catccgataa ggatatgtac cttgacaata gctccattga ggaagcttca    900
ggagtatatc ctattgatga tgatgactat tcttctgcct caggctcagg agctgatgaa    960
gacatagaga gtccagttct gacaacatcc caacctgcta taaaaagcac agatgtgtac   1020
acggagaaac attcagacaa tctgttttaa                                    1050
```

<210> SEQ ID NO 11
<211> LENGTH: 1149
<212> TYPE: DNA
<213> ORGANISM: Artificial sequence
<220> FEATURE:
<223> OTHER INFORMATION: DNA sequence of S2EDdeltaP124-F141 peptide used in the Examples

<400> SEQUENCE: 11

```
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg     300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600
tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtgatg acgacgacaa ggagacgaga    840
acagagctga catccgataa ggatatgtac cttgacaata gctccattga ggaagcttca    900
```

```
ggagtatatc ctattgatga tgatgactat tcttctgcct caggctcagg agctgatgaa    960
gacatagaga gtccagttct gacaacatcc caactgattc caagaatccc actcactagt   1020
gctgcttccc ccaaagtgga aaccatgacg ttgaagacac aaagcattac acctgctcag   1080
actgagtcac ctgaagaaac tgacaaggag gaagttgaca tttctgaggc agaagagaag   1140
ctgggctaa                                                           1149

<210> SEQ ID NO 12
<211> LENGTH: 1050
<212> TYPE: DNA
<213> ORGANISM: Artificial sequence
<220> FEATURE:
<223> OTHER INFORMATION: DNA sequence of S2EDdeltaL73-G123 peptide used
      in the Examples

<400> SEQUENCE: 12 atgtcccta tactaggtta ttggaaaatt aagggccttg tgcaacccac tcgacttctt     60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca    600 tggccttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtgatg acgacgacaa ggagacgaga    840
acagagctga catccgataa ggatatgtac cttgacaata gctccattga ggaagcttca    900
ggagtatatc ctattgatga tgatgactat tcttctgcct caggctcagg agctgatgaa    960
gacatagaga gtccagttct gacaacatcc caacctgcta taaaaagcac agatgtgtac   1020
acggagaaac attcagacaa tctgttttaa                                   1050
```

FRAGMENTS OF SYNDECAN-2 HAVING ANTI-ANGIOGENIC ACTIVITY

CROSS-REFERENCE TO RELATED APPLICATIONS

This application is a 35 U.S.C. § 371 national phase application of PCT Application No. PCT/GB15/53130, filed Oct. 20, 2015, which claims priority to Great Britain Application No. 1418562.3, filed Oct. 20, 2014, each of which is incorporated herein by reference in its entirety.

FIELD OF THE INVENTION

The present invention relates to anti-angiogenic peptides and their use in treating diseases associated with angiogenesis.

BACKGROUND

Angiogenesis is a physiological process involving activation of endothelial cells from a quiescent state to a migratory and proliferative phenotype in response to specific biological signals to form new blood vessels. It is an essential feature of growth and development, heart and kidney function and wound healing. Pathological angiogenesis is involved in a number of diseases such as cancer and inflammatory conditions such as rheumatoid arthritis and atherosclerosis. It plays a critical role in the growth and spread of cancer and is therefore a key target in cancer therapy.

New blood vessel formation entails proliferation of endothelial cells and remodelling of the extracellular matrix (ECM). Integrins, which play a major role in this response, exist in various activation states on the cell surface and modulate the migratory and adhesive characteristics of cells through interactions with the ECM. Other cell surface receptors also interact with ECM ligands leading to signalling cascades that can alter the activation state of integrins. Syndecans are an example of such molecules.

A number of inhibitors have been developed to suppress angiogenesis. For example, small molecules such as sorafenib and pazopanib inhibit kinases that promote angiogenesis; bevacizumab targets vascular endothelial growth factor (VEGF), a potent pro-angiogenic signalling molecule. There are however a number of serious side effects commonly associated with the use of anti-angiogenic compounds for example haemorrhage, hypertension, lymphopenia and diarrhea. In addition in the case of VEGF targeting therapies there is also a significant number of patient non-responders (~45%).

Thus there is a need for alternative therapies and methods for treating diseases associated with angiogenesis.

Syndecans are a family of transmembrane receptors with roles in cell adhesion, migration and growth factor signalling. Each syndecan molecule comprises a short highly conserved cytoplasmic domain, a transmembrane domain and a larger extracellular domain (ectodomain). In mammals, there are four syndecan family members—syndecans-1, -2, -3 and -4. In common with the other family members syndecan-2 has a short cytoplasmic domain, a single pass transmembrane domain and a larger extracellular domain which is substituted toward the N-terminus with heparan sulphate (HS) side chains and can be shed from the cell surface. Syndecan shedding is a feature of many cell types and occurs in response to stimuli such as inflammatory mediators and growth factors. Syndecan-2 and CD148 are molecules intimately associated with the vasculature. Syndecan-2 is expressed on fibroblasts, leukocytes and ECs and studies in zebrafish reveal syndecan-2 to be essential for branching angiogenesis.

A number of research groups have shown that syndecan-2 plays an important role in angiogenesis. For example, Chen et al (Blood; 103 (5); 1710-9; 2004); have shown that syndecan-2 is essential for angiogenic sprouting in zebrafish. Noguer et al (Experimental Cell Research, Vol 315: 5, 795-808, March 2009) have demonstrated that downregulation of syndecan-2 impairs angiogenesis in human microvascular endothelial cells.

The inventors have surprisingly found that a portion of the syndecan-2 molecule has an unexpected anti-angiogenic effect.

SUMMARY OF THE INVENTION

The present invention provides peptides with anti-angiogenic activity and nucleic acids that encode these peptides. The invention also provides methods, pharmaceutical compositions and kits for treating diseases associated with angiogenesis.

In a first aspect the invention provides an anti-angiogenic peptide comprising an amino acid sequence having at least 70% identity to amino acid residues 123-140 of SEQ ID NO 1 or amino acid residues 124-141 of SEQ ID NO 2.

DETAILED DESCRIPTION

"Angiogenesis" refers to the process of formation of new blood vessels. Angiogenesis requires the collective action of numerous pro- and anti-angiogenic factors to provide the signals necessary for the activation of endothelial cells to form new blood vessels. The angiogenic process involves a number of steps including enzymatic degradation of capillary basement membrane, endothelial cell (EC) proliferation and migration, invasion through the extracellular matrix and tubulogenesis.

"Tubulogenesis", or "tubule formation", as used herein refers to the development of endothelial cell tubes with an inner lumen generated by a polarised movement of the cells in response to pro-angiogenic signals.

"Anti-angiogenic activity" refers to suppression or inhibition of angiogenesis. "Anti-angiogenic peptides" are peptides that have anti-angiogenic activity.

A "peptide" refers to a chain of amino acid residues linked by peptide bonds. The terms "peptide" and "polypeptide" are used interchangeably.

Throughout this specification, amino acids may be referred to using the three letter and one letter codes as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and references to glutamic acid include glutamate, unless the context specifies otherwise.

In an embodiment of the invention, the peptide has at least 70% identity, at the amino acid level, to the sequences depicted in SEQ ID NO 1 or SEQ ID NO 2 or a fragment thereof, as defined herein.

SEQ ID NO 1 depicts the amino acid sequence of a human syndecan-2 molecule. SEQ ID NO 2 depicts the amino acid sequence of a mouse syndecan-2 molecule.

In an embodiment of the invention the anti-angiogenic peptide comprises an amino acid sequence having at least 70% sequence identity to amino acid residues 119-146 of SEQ ID NO 1 or amino acid residues 121-147 of SEQ ID NO 2. In a preferred embodiment the anti-angiogenic peptide comprises an amino acid sequence having at least 70% sequence identity to amino acid residues 120-144 of SEQ ID NO 1 or amino acid residues 121-145 of SEQ ID NO 2. In a preferred embodiment the anti-angiogenic peptide comprises an amino acid sequence having at least 70% sequence identity to amino acid residues 121-144 of SEQ ID NO 1 or amino acid residues 124-145 of SEQ ID NO 2. In a more preferred embodiment the anti-angiogenic peptide comprises an amino acid sequence having at least 70% sequence identity to amino acid residues 123-140 of SEQ ID NO 1 or amino acid residues 124-141 of SEQ ID NO 2.

In another embodiment of the invention, the peptide has at least 70% identity, at the amino acid level, to any of the amino acid sequences disclosed herein, for example the fragments of SEQ ID NO 1 or SEQ ID NO 2 referred to above and below or the sequences depicted in SEQ ID NO 3 or SEQ ID NO 4. More preferably, the peptides may have at least 75%, 80%, 85%, 90%, 91%, 92%, 93%, 94% and still more preferably at least 95%, 96%, 97% or 98% (still more preferably at least 99%) identity, at the amino acid level, to any of the amino acid sequences disclosed herein, for example the fragments of SEQ ID NO 1 or SEQ ID NO 2 referred to above and below or the sequences depicted in SEQ ID NO 3 or SEQ ID NO 4.

"Identity" as known in the art is the relationship between two or more polypeptide sequences or two or more polynucleotide sequences, as determined by comparing the sequences. In the art, identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984)), BLASTP, BLASTN, and FASTA (Atschul et al., J. Molec. Biol. 215, 403 (1990)).

Peptides for use in the invention may be identical to one or more of the amino acid sequences disclosed herein apart from the substitution of one or more amino acids with one or more other amino acids. The skilled person is aware that various amino acids have similar properties. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions. The present invention therefore extends to use of a peptide comprising an amino acid sequence described above but with one or more conservative substitutions in the sequence, such that the amino acid sequence has at least 70% identity to those described herein.

Peptides of the invention may have at least 70% sequence identity to amino acid residues 119-146, 120-144, 121-144 or 123-140 of SEQ ID NO 1 or amino acid residues 121-147, 121-145, 124-145 or 124-141 of SEQ ID NO 2. In preferred embodiments, the sequence identity is at least 75%, 80%, 85%, 90%, 91%, 92%, 93%, 94% and still more preferably at least 95%, 96%, 97% or 98% and still more preferably at least 99%.

In another embodiment the anti-angiogenic peptide consists of an amino acid sequence having at least 70% identity to amino acid residues 123-140 of SEQ ID NO 1 or amino acid residues 124-141 of SEQ ID NO 2.

In another embodiment the peptide comprises or consists of up to 25 amino acid residues and includes an amino acid sequence having at least 70% identity to amino acid residues 123-140 of SEQ ID NO 1 or amino acid residues 124-141 of SEQ ID NO 2.

The term "comprise" as used herein means that the claim encompasses all the listed elements or method steps, but may also include additional, unnamed elements or method steps. The peptide may comprise or consist of any of the amino acid sequences disclosed herein.

In a further embodiment the peptide comprises or consists of an amino acid sequence having at least 70% identity to up to 25 consecutive amino acid residues selected from: amino acid residues 120-144 of SEQ ID NO 1 or amino acid residues 121-145 of SEQ ID NO 2.

In a still further embodiment the peptide consists of an amino acid sequence having at least 70% identity to 25, 24, 23, 22, 21, 20, 19, 18, 17, or 16 amino acid residues, typically consecutive amino acid residues, selected from amino acid residues 119-146 of SEQ ID NO 1 or amino acid residues 121-147 of SEQ ID NO 2.

In a still further embodiment the peptide consists of an amino acid sequence having at least 70% identity to amino acid residues 123-140 of SEQ ID NO 1 or amino acid residues 124-141 of SEQ ID NO 2.

In all the embodiments described herein, the sequence identity may be at least 75%, 80%, 85%, 90%, 91%, 92%, 93%, 94% and still more preferably at least 95%, 96%, 97% or 98% and still more preferably at least 99%.

Peptides of the invention may be 15, 16, 17, 18, 19, 20, 21, 22, 23, 24 or 25 amino acid residues in length.

In a preferred embodiment the peptide is 16, 17, 18 or 19 amino acid residues in length.

In a more preferred embodiment the peptide is 18 amino acid residues in length.

In an embodiment of the first aspect of the invention the anti-angiogenic peptide is isolated. "Isolated" refers to material removed from its original environment. The original environment could be a natural environment for example inside a cell. An isolated peptide as used herein refers to a peptide which is at least 20% pure, preferably at least 40% pure, more preferably at least 60% pure, even more preferably at least 80% pure, most preferably at least 90% pure, and even most preferably at least 95% pure, as determined by SDS-PAGE.

In another embodiment the anti-angiogenic peptide of the invention may be fused to a heterologous peptide. A "heterologous peptide" as used herein refers to a peptide that imparts desired characteristics to the anti-angiogenic peptide for example increased stability, enhanced transport or simplified purification or detection. The heterologous peptide is typically not a syndecan or derived from a syndecan.

Examples of heterologous peptides intended for the purposes of the present invention include glutathione S-transferase, polyhistidine or myc tag to facilitate purification of the polypeptide for example by affinity chromatography. In another embodiment, the heterologous peptide is a fluorescent polypeptide. Fluorescent polypeptides include but are not limited to green fluorescent protein, red fluorescent protein, yellow fluorescent protein, cyan fluorescent protein and their derivatives.

Peptides of the invention may be produced by recombinant means, for example by expression of a nucleic acid construct as disclosed herein in a suitable vector, or by solid phase synthesis.

It should be appreciated that amino acid substitutions or insertions to the sequences disclosed herein that are within the scope of the present invention can be made using naturally occurring or non-naturally occurring amino acids. For example, D-amino acids can be incorporated in the peptides of the invention.

Peptides of the invention may be modified to improve their characteristics such as their half life, for example by PEGylation.

In a second aspect the invention provides a nucleic acid construct encoding an anti-angiogenic peptide according to the first aspect.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

In another embodiment of the invention, the nucleic acid has at least 70% identity, at the nucleic acid level, to any of the nucleic acid sequences disclosed herein, for example the sequences depicted in SEQ ID NO 8 or SEQ ID NO 9 or any fragment thereof, for example the sequences shown in bold and underline in FIG. 8 (nucleotides 367-420 of SEQ ID NO 8 or nucleotides 370-423 of SEQ ID NO 9). More preferably, the nucleic acid has at least 75%, 80%, 85%, 90%, 91%, 92%, 93%, 94% and still more preferably at least 95%, 96%, 97% or 98% (still more preferably at least 99%) identity, at the nucleic acid level, to any of the nucleic acid sequences disclosed herein, for example the sequences depicted in SEQ ID NO 8 or SEQ ID NO 9 or a fragment thereof, for example the sequences shown in bold and underline in FIG. 8 (nucleotides 367-420 of SEQ ID NO 8 or nucleotides 370-423 of SEQ ID NO 9).

The nucleic acid construct of the second aspect may be part of an expression cassette. An expression cassette is a part of a vector. It comprises a promoter, an open reading frame and a 3' untranslated region.

The nucleic acid construct of the second aspect of the invention may be in the form of or comprised within a vector. A vector as used herein refers to a construct for introducing a nucleic acid sequence into a cell or a virus for expression or replication. It refers to a recombinant construct for example a plasmid, a virus or any other construct capable of expression or replication of the nucleic acid sequence upon introduction into a cell or virus.

Examples of vectors include, among others, chromosomal, episomal and virus-derived vectors. Generally, any vector suitable to maintain, propagate or express nucleic acid to express a polypeptide in a host, may be used for expression in this regard.

The nucleic acid constructs and vectors of the invention may be present within a cell. As used herein, a cell refers to a prokaryotic cell, such as a bacterial cell, or eukaryotic cell, such as an animal, plant or yeast cell.

Diseases

The disease which can be treated/prevented by the compositions or methods of the present invention may be any disease associated with abnormal or excessive angiogenesis. A wide range of such diseases is listed by Carmeliet (Nature Medicine 9, 653-660 (2003)). Examples include cancer, arthritis, psoriasis, asthma and atherosclerosis. Angiogenesis is also a feature of ocular disease and is a major cause of blindness. It is a significant contributing factor in diabetic retinopathy, exudative (wet) or nonexudative (dry) age related macular degeneration (AMD), corneal graft rejection, corneal neovascularization, retinopathy of prematurity (ROP), retinal artery or vein occlusion, neovascular glaucoma and sickle cell retinopathy. Accordingly, the disease which can be treated/prevented by the compositions or methods of the present invention can be any of these diseases.

Pharmaceutical Compositions

In a third aspect the invention provides a pharmaceutical composition comprising a pharmaceutically acceptable carrier and an anti-angiogenic peptide according to the first aspect or a nucleic acid according to the second aspect.

In another embodiment the pharmaceutical composition further comprises an anti-angiogenic compound. Examples of anti-angiogenic compounds are known in the art such as suramin, sorafenib and sunitinib.

The pharmaceutical compositions of the invention may be used in the treatment of diseases associated with excessive or abnormal angiogenesis for example cancer, arthritis, psoriasis, asthma, atherosclerosis and ocular diseases such as diabetic retinopathy, exudative (wet) or nonexudative (dry) macular degeneration (AMD), corneal graft rejection, corneal neovascularisation, neovascular glaucoma, retinopathy of prematurity (ROP), retinal artery or vein occlusion and sickle cell retinopathy. In an embodiment of the invention the pharmaceutical compositions of the invention are for use in the treatment of cancer.

A pharmaceutical composition according to the present invention may be presented in a form that is ready for immediate use. Alternatively, the composition may be presented in a form that requires some preparation prior to administration.

Pharmaceutical compositions of the invention may be adapted for administration by any appropriate route, for example by the oral (including buccal or sublingual), topical (including buccal, sublingual or transdermal), or parenteral (including subcutaneous, intramuscular, intravenous, intraperitoneal or intradermal) route.

The pharmaceutically acceptable carrier that is present in the pharmaceutical compositions of the invention may be any suitable pharmaceutically acceptable carrier or excipient that is known in the art.

Pharmaceutical compositions adapted for parenteral administration may include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents.

Excipients which may be used for injectable solutions include water, alcohols, polyols, glycerine and vegetable oils, for example. The compositions may be presented in unit-dose or multidose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the peptide or nucleic acid construct of the present invention.

Methods of Treatment

In a fourth aspect the invention provides a method of treating a disease associated with (abnormal or excessive) angiogenesis comprising administering to a subject in need thereof a therapeutically effective amount of an anti-angiogenic peptide of the first aspect, a nucleic acid construct of the second aspect or a pharmaceutical composition of the third aspect.

A therapeutically effective amount is the dose sufficient to reduce or inhibit angiogenesis.

In an embodiment of the invention the method of treatment comprises administering peptides, nucleic acid construct and/or pharmaceutical compositions of the invention in combination with other anti-angiogenic therapy.

In an embodiment of the invention the method is for treating a disease such as cancer, arthritis, psoriasis, asthma, atherosclerosis and ocular diseases such as diabetic retinopathy, exudative (wet) or nonexudative (dry) macular degeneration (AMD), corneal graft rejection, corneal neovascularisation, retinopathy of prematurity (ROP), neovascular glaucoma, retinal artery or vein occlusion and sickle cell retinopathy. In a further embodiment the method is for treating cancer.

As used herein, a subject refers to an animal, including a human being. An animal can include mice, rats, fowls such as chicken, ruminants such as cows, goat, deer, sheep and other animals such as pigs, cats, dogs and primates such as humans, chimpanzees, gorillas and monkeys. Preferably the subject is human.

This aspect of the invention also extends to:

An anti-angiogenic peptide of the first aspect, a nucleic acid construct of the second aspect or a pharmaceutical composition of the third aspect for use in the treatment of a disease associated with angiogenesis.

Use of an anti-angiogenic peptide of the first aspect, a nucleic acid construct of the second aspect or a pharmaceutical composition of the third aspect in the manufacture of a medicament for the treatment of a disease associated with angiogenesis.

As used herein, "treatment" is also intended to cover preventative treatment, i.e. prophylaxis.

Dosages

A therapeutically effective amount is the dose sufficient to reduce or inhibit angiogenesis.

Doses for delivery and administration can be based upon current existing protocols, empirically determined, using animal disease models or optionally in human clinical trials. Initial study doses can be based upon animal studies set forth herein, for a mouse, for example.

Doses can vary and depend upon whether the treatment is prophylactic or therapeutic, the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled person will appreciate the factors that may influence the dosage and timing required to provide an amount sufficient for providing a therapeutic or prophylactic benefit.

Combination Therapy

Treatment of a disease associated with angiogenesis may be carried out by combining a peptide of the invention with other anti-angiogenic agents. For example, tumours may be treated by administering peptide therapy in conjunction with compounds such as suramin, sorafenib, sunitinib, pazopanib, everolimus, bevacizumab, IL-12, IFN-$\alpha$, angiostatin and prolactin. This list is non-exhaustive and alternatives are well known in the art. Peptide therapy may be combined with other therapies for example chemotherapy, radiotherapy or immunotherapy.

Kit of Parts

In a fifth aspect the invention provides a kit or kit of parts comprising peptides, nucleic acid constructs and/or pharmaceutical compositions of the invention.

In an embodiment of the invention the kit is for use in the treatment of diseases associated with angiogenesis, as defined herein. In a preferred embodiment the kit is for use in the treatment of cancer.

The kit may include a sealed container containing the peptide of the invention as a lyophilized powder and a second container containing a solvent. The peptide may be freeze dried. Further components may be included with the solid or liquid part. Thus the kit may comprise a first container containing the peptide and a second containing isotonic saline, or a first container containing the peptide and mannitol and a second container containing sterile water. Prior to administration the solvent is added to the container containing solid component in order to give the solution for injection. The kit may include instructions for use.

Preferred features of the second and subsequent aspects of the invention are as described for the first aspect of the invention mutatis mutandis.

The invention will now be further described by way of reference to the following Examples which are present for the purposes of reference only and are not to be construed as being limiting on the invention.

Reference is made to a number of drawings in which:

FIG. 1 shows scratch wound cell migration assay. In this assay scratches are made in confluent monolayers of HUVECS and the cells incubated in the presence or absence of different concentrations of the human syndecan-2 peptides. Cell migration is measured by time lapse microscopy using an Olympus IX81 microscope with a controlled environment chamber set at 37° C., 10% $CO_2$. Images were captured every 30 minutes using a Hamamatsu Orca ER digital camera and processed using Cell^M software (Olympus). (A) Phase contrast micrographs of scratch wounds after 9 hours of incubation post scratch. (B) The area migrated by HUVECs was calculated using IMAGEJ software to measure the migrated area at time=0 and time=9 hours. The 0 hour value was then subtracted from the 9 hour value.

FIG. 2 shows cell migration in murine EC cells in response to different murine syndecan-2 fusion proteins. Scratch wound migration assays were performed in the presence of 0.5 μM of the fusion proteins indicated on brain ECs. Cell migration is measured by time lapse microscopy using an Olympus IX81 microscope with a controlled environment chamber set at 37° C., 10% $CO_2$. Images were captured every 30 minutes using a Hamamatsu Orca ER digital camera and processed using Cell^M software (Olympus). (A) Phase contrast images 9 hours after the scratch was made. (B) EC migration speed is reduced in the presence of S2ED proteins containing the 18aa regulatory domain. Cell speed data represents mean measurements from at least 25 individual cells at the leading edge per treatment.

FIG. 3 shows microtubule formation in human EC. 80,000 HUVECs were seeded into 24 well plates coated with 100 μl/well of growth factor depleted Matrigel (BD Sciences) in the presence of the human syndecan-2 peptides scr or hS2pep at the concentrations indicated (scr corresponds to a scrambled control peptide). Tubule formation was monitored by time lapse microscopy using an Olympus IX81 microscope with a controlled environment chamber set at 37° C., 10% $CO_2$. Images were captured every 30 minutes using a Hamamatsu Orca ER digital camera and processed using Cell^M software (Olympus). (A) Phase contrast images of tubules after 6 hours in culture. (B) Branch points were counted on at least four representative images. A branch point is defined at which two or more tubules meet.

FIG. 4 shows angiogenic sprouting in rat ECs. (A) Diagram of the murine syndecan-2 mutant proteins used in this study. (B) Rat aortas were seeded in collagen I matrices as above containing 0.5 μM of GST(control), S2ED or the mutant forms of S2ED. Sprouts from 8 rings per condition were counted and the mean calculated. Error bars represent the SEM and significance was calculated using a one way ANOVA with Bonferroni multiple comparison (p*<0.005, p**<0.0001).

FIG. 5 shows murine skin EC invasion through Collagen I. 10 μl of Collagen I matrices (1 mg/ml in E4 media) containing 1 μM of human syndecan-2 peptide (hS2pep) and control (scr) in an 8μ transwell were prepared. 50,000 skin ECs were seeded and cells which had passed through the matrix were counted after 24 hours. Cells were stained with Calcein (5 μM) and cells imaged using an Olympus IX81 inverted microscope and a Hamamatuse Orca ER digital camera. Fluorescent cells are shown in (A) and the % migrated cells compared to the untreated control is shown in B. Cell numbers were counted from four independent images and error bars represent the SEM. Significance was calculated using 1 way ANOVA with Tukey's multiple comparison p<0.0001).

FIG. 6 shows S2ED interaction with CD148 resulting in angiogenesis. (A) bEND3.1, MLEC and sEND cells express CD148. Western blot of lysates from the EC lines indicated were probed with antibodies to CD148 or β-tubulin. (B) CD148 interacts with murine syndecan extracellular core protein (S2ED). Cell lysates from sEND cells were incubated with beads coated with GST(control), S2ED, S2EDΔ$P^{124}$-$F^{141}$ or S2EDΔ$L^{73}$-$G^{123}$. Precipitates were analysed by Western blot for the presence of CD148. CD148 was only pulled down by forms of S2ED which contain the C-terminal 18 amino acid adhesion regulatory domain. Blot is representative of 4 experiments.

FIG. 7 shows the amino acid sequences of the peptides referred to herein. SEQ ID NO 1 depicts the amino acid sequence of a full length human syndecan-2 molecule. SEQ ID NO 2 depicts the amino acid sequence of a full length mouse syndecan-2 molecule. Amino acid residues 123-140 of SEQ ID NO 1 and amino acid residues 124-141 of SEQ ID NO 2 are shown in bold. SEQ ID NOs 3 to 7 correspond to the peptides and proteins used in the Examples. In SEQ ID NOs 3 to 5 the amino acid sequence of the GST+linker is shown in underline and in SEQ ID NOs 3 and 5 the 18 amino acid peptide (corresponding to amino acid residues 124-141 of SEQ ID NO 2) is shown in bold.

FIG. 8 shows the coding sequence (nucleic acid sequence) of human Syndecan-2 (SEQ ID NO 8) and murine Syndecan-2 (SEQ ID NO 9). DNA sequence in bold and underline in SEQ ID NO 8 corresponds to (encodes) the peptide of the invention having the amino acid sequence of amino acid residues 123-140 of SEQ ID NO 1 and DNA sequence in bold and underline in SEQ ID NO 9 corresponds to (encodes) the peptide of the invention having the amino acid sequence of amino acid residues 124-141 of SEQ ID NO 2. SEQ ID NOs 10 to 12 are the DNA sequences of peptides and proteins used in the Examples.

EXAMPLES

1. Inhibition of Endothelial Cell Migration

Figure 9:
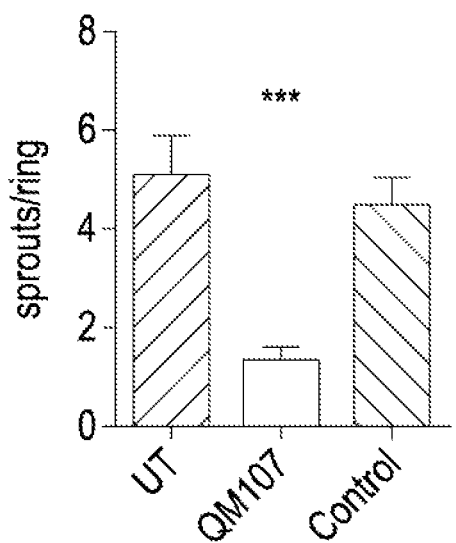
FIG. 9 shows that QM107 (HS2pep; SEQ ID NO 6) inhibits angiogenic sprout formation in the mouse aortic ring model.

Endothelial cell (EC) migration is a critical process in angiogenesis. The following series of experiments aimed to investigate the effect of human and murine syndecan-2 peptides on this response.

In one assay, scratches were made in confluent monolayers of HUVECs and the cells incubated in the presence or absence of different concentrations of hS2pep (human syndecan-2 peptide) and scrambled peptides (FIG. 1A). The hS2pep significantly inhibited HUVEC cell migration after 4 hours in culture. Scratch wound closure was greatly reduced in 1 uM hS2pep treated cells indicating an inhibition of EC migration (FIG. 1B).

Migration assays were also performed on brain ECs in the presence of murine syndecan-2 GST fusion proteins—either S2ED or the truncated forms of this protein (S2EDΔ$P^{124}$-$F^{141}$ and S2EDΔ$L^{73}$-$G^{123}$). As found with the full length protein, the truncated fusion protein containing only the adhesion regulatory domain (S2EDΔ$L^{73}$-$G^{123}$), inhibited EC cell migration (FIGS. 2A and B). In contrast, the mutant protein lacking the syndecan-2 adhesion regulatory domain did not affect cell migration, with wound closure being equivalent to that noted with cells treated with GST alone.

2. Inhibition of Capillary Network Formation

The ability to form a capillary network to supply blood and remove waste products is essential for the successful growth and development of solid tumours. Consequently, the ability of ECs to form a capillary network when seeded on Matrigel is also proposed to be a good indicator of the angiogenic potential of cells.

To investigate the inhibitory effect of peptides derived from human syndecan-2, 80,000 HUVECs were seeded into 24 well plates coated with 100 ul/well of growth factor depleted Matrigel in the presence of scr or hS2pep. Tubule formation was monitored by time lapse microscopy (FIG. 3A). FIG. 3B shows that capillary network formation was inhibited in the presence of hS2pep (1 µm) particularly when the number of branch points was taken as a measure.

In another assay with murine peptides, full length S2ED, S2EDΔ$P^{124}$-$F^{141}$ (lacking adhesion regulatory domain) or S2EDΔ$L^{73}$-$G^{123}$ (truncated form containing only the adhesion regulatory residues) were incorporated into collagen matrices in which aortic ring sections were embedded (FIGS. 4A and B). Whilst angiogenic sprouts were observed in both untreated and GST controls, sprout formation was severely compromised when rings were embedded in matrices with S2ED or S2EDΔ$L^{73}$-$G^{123}$ both of which contain the regulatory 18 amino acid motif motif (FIG. 4B). These data indicate that the anti-angiogenic properties of S2ED are dependent on the adhesion regulatory domain lying between $P^{124}$ and $F^{141}$ of murine syndecan-2.

3. Inhibition of Endothelial Cell Invasion

Invasion through the extracellular matrix is another indicator of angiogenesis. Collagen I matrices containing 1 uM of hS2pep and scr were prepared in an 8 ul transwell. 50,000 murine skin ECs were seeded and cells which had passed through the matrix were counted after 24 hours. FIG. 5 shows that invasion through collagen I was inhibited by the presence of hS2pep (1 uM).

4. The Inhibition of Angiogenesis by S2ED is Driven by CD148 Leading to Changes in β1 Integrin Activation In fibroblasts the protein tyrosine phosphatase receptor CD148 interacts directly with the adhesion regulatory domain of S2ED leading to β1 integrin mediated cell attachment and spreading (Whiteford et al., 2011 Mol Biol Cell, 22(19):3609-24). To determine whether CD148 is a mediator for EC responses to S2ED the expression of CD148 on ECs from brain, lung and skin was confirmed. Western blot analysis using an antibody directed to the cytoplasmic domain of CD148 revealed that all three cell lines expressed this receptor (FIG. 6A). The interaction between CD148 and the syndecan-2 ectodomain was demonstrated by performing a pull down assay using GST-S2ED beads as bait. No CD148 was evident in precipitates in which GST or GST-S2EDΔ$P^{124}$-$F^{141}$ coated beads were used (FIG. 6B). S2ED and S2EDΔ$L^{73}$-$G^{123}$, which both contain the C-terminal 18aa adhesion regulatory domain successfully pull-down CD148 from EC lysates indicating that the interaction point between CD148 and S2ED resides in this region of the molecule.

Materials and Methods
Fusion Proteins and Antibodies:

Peptides derived from murine syndecan-2: S2ED (SEQ ID NO 3), S2EDΔ$P^{124}$-$F^{141}$ (SEQ ID NO 4) and S2EDΔ$L^{73}$-$G^{123}$ (SEQ ID NO 5).

Peptides derived from human syndecan-2: hS2pep (SEQ ID NO 6) and scr (SEQ ID NO 7).

"scr" is a scrambled peptide used as a negative control.

The sequences of the peptides are shown in FIG. 7.

Peptides and soluble CD148 were purified as described previously (Whiteford et al., 2011). Antibodies used were anti-CD148 (R and D Systems), anti β-tubulin (clone TUB2.1, Sigma), Phalloidin 568 (Life Technologies.

Cell culture: All cells used in this study were grown at 37° C., 10% $CO_2$ in DMEM (PAA), supplemented with 10% FBS, 2 mM L-glutamine, 1% non-essential amino acids, 1 mM sodium pyruvate and 5 µM β-mercaptoethanol (All Invitrogen). Primary murine lung ECs were isolated and maintained as described in Reynolds et al. (Nature Medicine 8:27-34, 2002). HUVECs (HPA Laboratories) were grown and maintained in Endothelial Growth Medium (HPA Laboratories) and maintained as above.

Generation of syndecan-2 expressing cell lines: Gene synthesis of the complete murine syndecan-2 cDNA and the cDNA encoding only the syndecan-2 ectodomain coding sequence was performed by GeneArt (Invitrogen). Both full length and truncated syndecan-2 cDNAs were mutated such that the HA epitope was inserted between D27 and K28. BamHI sites were also incorporated at the 5' and 3' of the two synthetic genes. The cDNAs were cloned into the BamHI site of the lentiviral vector pLNT-SFFV-MCS-EGFP (provided by T. R Mckay, St Georges Medical School, London). Lentiviruses were produced in HEK293t cells and packaged into a VSVG coat using conventional procedures. HEK293t cells were transfected using the supernatant transfer method. Cells expressing high levels of eGFP were sorted by flow cytometry and these were cultured in DMEM as described.

Matrigel plug assay: Male C57BL/6 mice (6 week old) were given subdermal abdominal injections consisting of 600 µl of Matrigel (BD Biosciences) mixed with 100 µl of PBS containing 100 ng/ml VEGF, 100 ng/ml FGF and 20 U/ml of heparin and 0.5 µM of either GST or S2ED (following the method described in Passaniti et al. (Laboratory Investigation 67:519-528, 1992). Mice were sacrificed after three days and the plugs excised, photographed and incubated overnight in PBS. Haemoglobin was quantified using Drabkin's reagent (Sigma) as described by the manufacturer. All experiments were performed under the UK legislation for the protection of animals, and at the end of all in vivo procedures involving anaesthesia, animals were humanely killed by cervical dislocation in accordance with UK Home Office regulations. Excised plugs were frozen in liquid nitrogen and subsequently embedded in ice cold OCT, 15 µm sections were made using a cryostat at −20° C. Following fixation with 4% PFA for 5 min and blocking with 10% Normal Goat Serum for 15 min, sections were stained for nuclei (DRAQ5) and the EC marker CD31 overnight. Images were captured using a PASCAL laser-scanning confocal microscope (Carl Zeiss, 10× objective). Quantification was performed using the IMARIS software and Photoshop (Adobe), ECs were identified by co-localization of nuclei with CD31 staining.

Aortic ring assay: Thoracic aortas dissected from cervically dislocated 180-200 g male wistar rats (Harlan Laboratories) or 6 week old C57BL/6 mice (Charles River) were sliced into 0.5 mm sections and incubated overnight in serum free OptiMEM (Invitrogen) at 37° C. Aortic rings were embedded in type I collagen (1 mg/ml) in E4 media (Invitrogen) containing either GST, syndecan-2 mutant proteins or peritoneal exudates in 48 well plates. Wells were supplemented with OptiMEM with 1% FBS and 10 ng/ml VEGF (R and D systems, 30 ng/ml for murine rings) and incubated at 37° C., 10% CO2. Angiogenic sprouts from rat and mouse aortas were counted after 4 days and 8 days respectively (Method based on that of Nicosia and Ottinetti (Laboratory Investigation 63:115-122, 1990) and modified in De Rossi et al. (Journal of Genetic Syndromes & Gene Therapy 4, 2013).

In vitro tubule formation assays: HUVEC and human dermal fibroblasts were co cultured using the Cell Works V2a kit (Caltag Media Systems as described by the manufacturers). Medium containing control compounds, GST or S2ED was changed every second day and at day 14 ECs were stained for CD31 to assess the tube formation. Imaging was performed using an Olympus IX81 inverted microscope (10× objective), tube length and branch points were quantified using Photoshop (Adobe). A branch point is defined as the point at which two or more tubules meet and the tubule length is the length of tubules between branch points. In a second type of microtubule assay sEND cells ($5 \times 10^4$) were seeded into 24 well plates coated with 150 µl of Matrigel (BD Sciences) in the presence of either GST or S2ED. Using the Cell-IQ controlled environmental chamber (CM Technologies) plates were incubated at 37° C., 10% CO2 and images were captured every 15 minutes for 16 hours.

Scratch wound migration assays: Scratch wound migration assays were performed on confluent monolayers of ECs. Wounds were made using a pipette tip, and fusion proteins were added to the medium and images were captured every 30 minutes for 12 hours by time lapse microscopy using an Olympus IX81 microscope. Percentage wound closure was calculated and individual cells tracked using Image J.

Invasion assay: Invasion assays through collagen and Matrigel matrices were performed in 24-well plates with transwell inserts (Millipore; 8 µm pore size, polyester (PET) membrane). Membranes were coated with 10 µl of a Collagen Type I mixture (Millipore; 1 mg/ml in E4 medium) containing 0.5 µM GST or S2ED. sEND cells were seeded on the gel in a homogenous single cell suspension of 5,000 cells/insert in 200 µl of DMEM+10% FBS; 1 ml of the same medium was added to the bottom well. Invasion was measured after 6 hours after which time gels were removed with a cotton swab, the filter washed in PBS and stained with calcein (Invitrogen) and the number of cells attached to the filter was counted.

Proliferation: Cell proliferation was measured using the CellTiter 96 AQueous Cell proliferation assay kit as described by the manufacturer (Promega).

CD148 pulldown and Western blot: Confluent bEND3.1 cells were lysed in 1% tritonx100 in TBS containing HALT protease and phosphatase inhibitors (Pierce). GST and S2ED were bound to glutathione-sepharose beads (GE Healthcare) and were added to cell lysates and incubated for 1 hour. Beads were isolated by centrifugation and washed twice in TBS, prior to incubation in Laemmli buffer and analysis by Western blot using standard procedures.

Dot Blotting: Samples were diluted in blotting buffer (0.15 M NaCl buffered to pH 4.5 with 50 mM sodium acetate, and with 0.1% Triton X-100) and applied under vacuum to cationic nylon membranes (GE; Amersham Hybond™-N+). Membranes were washed three times with blotting buffer, blocked for 1 h in blocking buffer (3% milk, 0.5% BSA, 0.15 M NaCl in 10 mM TRIS, pH 7.4), incubated over night with primary antibody in blocking buffer plus 0.3% Tween-20. After washing blots were incubated for 2 hrs with the appropriate HRP-conjugated secondary antibody and signals were detected by chemi-luminescence using conventional procedures. Quantification of the signal intensity was performed using ImageJ software.

FACS and immuno-fluorescent staining for active integrin: Confluent bEND3.1 cells were trypsinised and the trypsin inactivated with BSA. Cells were re-suspended in Hank's buffer (without calcium and magnesium) containing the treatments described (0.5 µM GST or S2ED) and incubated for 30 minutes at 37° C. Cells were then fixed in 2% PFA prior to FACS analysis for both total and active β1 integrin and the percentage of cells expressing active β1 calculated. For immuno-fluorescent staining of active β1 integrin confluent monolayers of sEND cells were grown on microscope slides and scratch wounds were performed and either 0.5 µM GST or S2ED was added. After 30 mins cells were fixed with 4% paraformaldehyde (Sigma) and permeabilised in 0.1% Triton X100 (Sigma) in PBS. Samples were incubated with active β1 integrin specific antibody 9EG7 in 1% normal goat serum in PBS overnight at 4° C. Slides were washed in PBS and incubated in anti-rabbit IgGs alexafluor 488 (Molecular Probes) and DAPI and images were captured on an Olympus IX81 inverted microscope. Fluorescent intensity profiles from the resultant images were calculated using IMAGEJ. For higher resolution images cells were imaged using a PASCAL laser-scanning confocal microscope (Carl Zeiss) with a 63× objective and the resultant stacks were processed using IMARIS software. HUVECS were seeded on coverslips coated with fibronectin (10 µg/ml) and Collagen I (30 µg/m) in 0.1% gelatin. Once ~60% confluent, cells were washed with SF OptiMEM then treated either with or without 1 mM MnCl2 in the presence of either 0.5 µM GST or S2ED for 30 mins. Cells were then fixed in 2% PFA and stained using a monoclonal active β1 integrin specific antibody (clone HUTS4, dil. 1:300). After washing cells were stained with an anti-mouse IgGs conjugated to alexafluor 594 (Molecular Probes). Cells were analysed by confocal microscopy as described above.

5. QM107 (HS2pep) Inhibits Angiogenic Sprout Formation in the Mouse Aortic Ring Model.

Methodology:

Already Described

Results:

In FIG. 9 we show that angiogenic sprout formation is inhibited in the presence of 0.5 µM of QM107 (Development name for our peptide aka HS2pep) using the murine aortic ring models of angiogenesis. The peptide was added to the medium and sprouts were counted after 7 days in culture. Data represents the mean of at least 15 rings and error bars represent the SEM. Significance is indicated on the basis of a non-paired students t test ($p^{***}<0.001$).

6: QM107 (HS2pep) Inhibits Angiogenic Sprout Formation in the Choroid Explant Model.

Methodology:

18 day old C57BL6 mice were sacrificed by cervical dislocation and eyes were enucleated prior to an incision being made 1 mm below the iris and removal of the iris, cornea lens and retina. The choroid is then removed flattened and cut into 1 mm pieces prior to incubation in serum free OptiMEM o/n at 37° C. Choroid explants are then embedded in a Collagen I matrix containing scrambled or experimental peptides and supplemented with OptiMEM containing 10 ng/ml murine VEGFA. Angiogenic sprouts were counted after 7 days.

Figure 10:
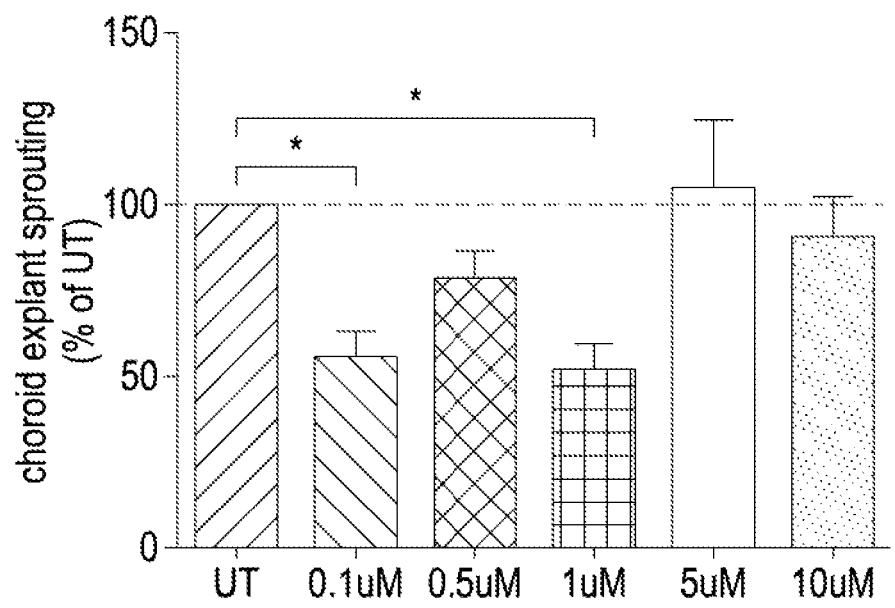
FIG. 10 shows that QM107 (HS2pep; SEQ ID NO 6) inhibits angiogenic sprout formation in the choroid explant model.

Results:

The choroid is a vascular bed beneath the retinal pigment epithelium and supplies oxygen and nutrients to the outer retina. The choroid can be readily isolated from the murine eye and when placed in a suitable medium and after 4-6 days in culture vessel sprouting occurs and can be quantified. This assay recapitulates Choroidal neovascularisation, the cause of central vision loss in wet Age Related Macular Degeneration. FIG. 10 shows that at doses ranging from 0.1 µM to 1 µM inhibit the formation of angiogenic sprouts in this model. Data is the mean number of sprouts from at least 6

Choroid explants from a total of 8 animals. Error bars represent the SEM and significance was calculated using a students t test p<0.05.

7: QM107 (HS2pep) Inhibits Choroidal Neo-Vascularisation In Vivo.

Methodology: Day 0 (27/7):

6 Week old C57BL mice were anaesthetised on day 0 and 3 laser burns were applied to both eyes. On day 3, 1 μl of 4 μM QM107 (hS2pep), PBS or 4 μM scrambled control were injected into both eyes of the animals. On day 7 the choroidal neovascularisation, in response to the laser lesion, were observed by fluorescein angiography. The area of Choroidal neovascularistaion was then calculated by analysis of images using IMAGEJ.

Figure 11:
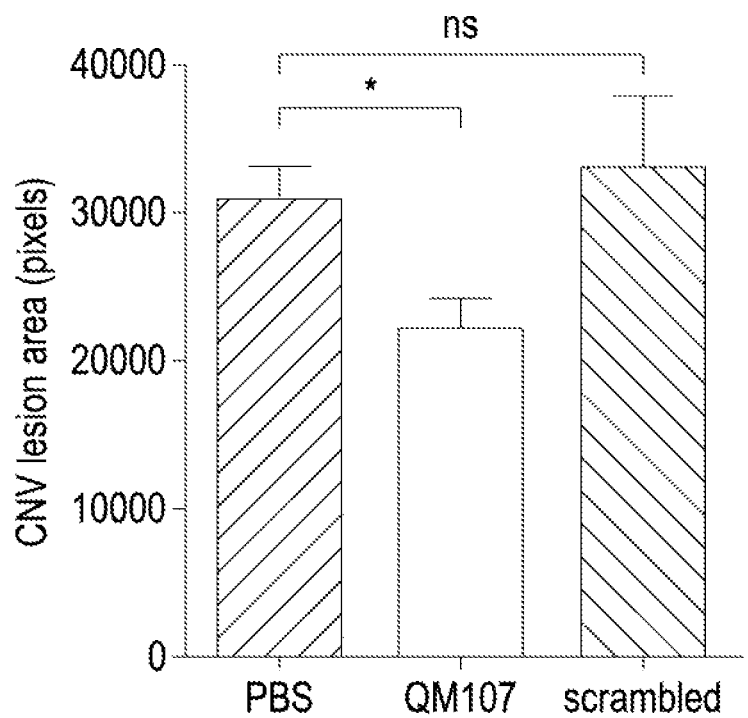
FIG. 11 shows that QM107 (HS2pep; SEQ ID NO 6) inhibits choroidal neo-vascularisation in vivo.

Results:

QM107 (hS2pep) shows efficacy in an in vivo model of choroidal neovascularisation. C57BL mice were treated as described above and it is evident from FIG. 11 that around 30% less choroidal neovascularisation occurs in mice treated with 1 μM of QM107 7 days post injury as compared to animals treated with PBS or the scrambled control. N=10 for each condition and significance was calculated using a students t test.

8: QM107 (hs2pep) Inhibits Angiogenesis in the Matrigel Plug Assay

Methodology:

Already Described

Figure 12:
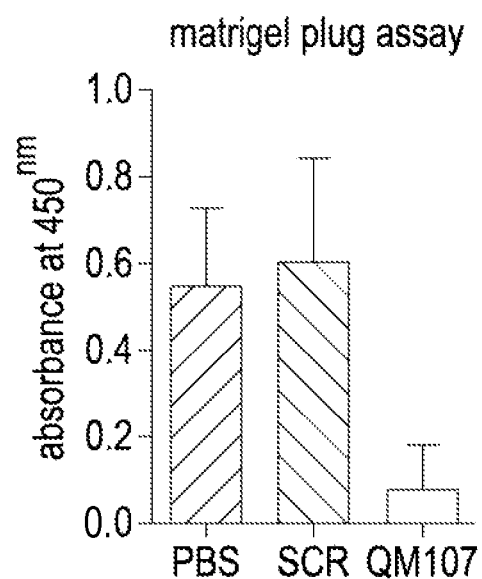
FIG. 12 shows that QM107 (HS2pep; SEQ ID NO 6) inhibits angiogenesis in the matrigel plug assay.

Results:

The haemoglobin content of Matrigel plugs injected under the skin in the flank of C57BL6 mice is greatly reduced when 50 μM QM107 is incorporated as compared to a scrambled peptide control or PBS, as shown in FIG. 12. Data is from 2 plugs per animal and is the mean of two measurements.

---

The invention claimed is:

1. An anti-angiogenic peptide consisting of up to 25 amino acids comprising a) amino acid residues 123-140 of SEQ ID NO 1 or amino acid residues 124-141 of SEQ ID NO 2, or b) amino acid residues 123-140 of SEQ ID NO 1 and having conservative amino acid substitutions at one or more positions selected from the group consisting of E125, E126, D127, N129, and S138, or amino acid residues 124-141 of SEQ ID NO 2 and having conservative amino acid substitutions at one or more positions selected from the group consisting of I126, K127, S128, D130, and N139.

2. The anti-angiogenic peptide according to claim 1, wherein the peptide consists of 18 or 19 amino acids and includes a) amino acid residues 123-140 of SEQ ID NO 1 or amino acid residues 124-141 of SEQ ID NO 2, or b) amino acid residues 123-140 of SEQ ID NO 1 and having conservative amino acid substitutions at one or more positions selected from the group consisting of E125, E126, D127, N129, and S138, or amino acid residues 124-141 of SEQ ID NO 2 and having conservative amino acid substitutions at one or more positions selected from the group consisting of I126, K127, S128, D130, and N139.

3. The anti-angiogenic peptide according to claim 1, wherein the peptide comprises up to 25 consecutive amino acid residues selected from: a) amino acid residues 120-144 of SEQ ID NO 1 or amino acid residues 121-145 of SEQ ID NO 2, or b) amino acid residues 120-144 of SEQ ID NO 1 and having conservative amino acid substitutions at one or more positions selected from the group consisting of E125, E126, D127, N129, and S138, or amino acid residues 121-145 of SEQ ID NO 2 and having conservative amino acid substitutions at one or more positions selected from the group consisting of I126, K127, S128, D130, and N139.

4. The anti-angiogenic peptide according to claim 3, wherein the peptide consists of amino acid residues 123-140 of SEQ ID NO 1 or amino acid residues 124-141 of SEQ ID NO 2.

5. The anti-angiogenic peptide according to claim 1 wherein the peptide is fused to a heterologous peptide.

6. A nucleic acid construct encoding the anti-angiogenic peptide according to claim 1.

7. A vector comprising a nucleic acid construct according to claim 6.

8. A cell comprising a nucleic acid construct according to claim 6.

9. A pharmaceutical composition comprising a pharmaceutically acceptable carrier and an anti-angiogenic peptide according to claim 1 or a nucleic acid construct encoding an anti-angiogenic peptide according to claim 1.

10. A pharmaceutical composition according to claim 9 further comprising an anti-angiogenic compound.

11. A pharmaceutical composition according to claim 10 wherein the anti-angiogenic compound is selected from the group consisting of suramin, sorafenib and sunitinib.

12. A method for the treatment of a disease associated with angiogenesis comprising administering to a subject in need thereof a therapeutically effective amount of an anti-angiogenic peptide according to claim 1, or a nucleic acid construct encoding an anti-angiogenic peptide according to claim 1.

13. The method according to claim 12 wherein the disease is cancer, arthritis, psoriasis, asthma, atherosclerosis or an ocular disease.

14. A kit comprising an anti-angiogenic peptide according to claim 1, or a nucleic acid construct encoding an anti-angiogenic peptide according to claim 1.

15. A cell comprising a vector according to claim 7.

16. A method for the treatment of a disease associated with angiogenesis comprising administering to a subject in need thereof a therapeutically effective amount of a pharmaceutical composition according to claim 9.

17. The method according to claim 13 wherein the ocular disease is selected from the group consisting of diabetic retinopathy, exudative (wet) or nonexudative (dry) macular degeneration (AMD), corneal graft rejection, corneal neovascularisation, retinopathy of prematurity (ROP), retinal artery or vein occlusion, neovascular glaucoma, and sickle cell retinopathy.

18. A kit comprising a pharmaceutical composition according to claim 9.

19. An anti-angiogenic peptide consisting of up to 25 amino acids comprising: a) amino acid residues 123-140 of SEQ ID NO 1 or amino acid residues 124-141 of SEQ ID NO 2, or b) amino acid residues 123-140 of SEQ ID NO 1 and having one conservative amino acid substitution therein, or amino acid residues 124-141 of SEQ ID NO 2 and having one conservative amino acid substitution therein.

20. The anti-angiogenic peptide according to claim 19, wherein the peptide consists of 18 or 19 amino acids and includes: a) amino acid residues 123-140 of SEQ ID NO 1 or amino acid residues 124-141 of SEQ ID NO 2, or b) amino acid residues 123-140 of SEQ ID NO 1 and having one conservative amino acid substitution therein or amino acid residues 124-141 of SEQ ID NO 2 and having one conservative amino acid substitution therein.

21. The anti-angiogenic peptide according to claim 19, wherein the peptide comprises up to 25 consecutive amino acid residues selected from: a) amino acid residues 120-144 of SEQ ID NO 1 or amino acid residues 121-145 of SEQ ID NO 2, or b) amino acid residues 120-144 of SEQ ID NO 1 and having one conservative amino acid substitution therein or amino acid residues 121-145 of SEQ ID NO 2 and having one conservative amino acid substitution therein.

* * * * *